US011172853B2

(12) United States Patent
Hamade et al.

(10) Patent No.: US 11,172,853 B2
(45) Date of Patent: Nov. 16, 2021

(54) BIOLOGICAL INFORMATION ACQUISITION DEVICE AND BIOLOGICAL INFORMATION ACQUISITION METHOD

(71) Applicant: SEIKO EPSON CORPORATION, Tokyo (JP)

(72) Inventors: Yuiga Hamade, Chino (JP); Tetsuji Fujita, Chino (JP); Takashi Toya, Chino (JP); Yasunori Koide, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 470 days.

(21) Appl. No.: 16/305,573

(22) PCT Filed: May 18, 2017

(86) PCT No.: PCT/JP2017/018655
§ 371 (c)(1),
(2) Date: Nov. 29, 2018

(87) PCT Pub. No.: WO2017/208840
PCT Pub. Date: Dec. 7, 2017

(65) Prior Publication Data
US 2019/0298238 A1    Oct. 3, 2019

(30) Foreign Application Priority Data

May 30, 2016 (JP) .............................. JP2016-107006

(51) Int. Cl.
*A61B 5/1455* (2006.01)
*A61B 5/145* (2006.01)
(52) U.S. Cl.
CPC ........ *A61B 5/14552* (2013.01); *A61B 5/1455* (2013.01); *A61B 5/14532* (2013.01)

(58) Field of Classification Search
CPC .............. A61B 5/1455; A61B 5/14551; A61B 5/14552; A61B 5/14532
See application file for complete search history.

(56) References Cited

U.S. PATENT DOCUMENTS 7,596,398 B2 *  9/2009  Al-Ali ................. A61B 5/7221
                                                        600/344
2012/0236310 A1 *  9/2012  Lesage ................ A61B 5/0091
                                                        356/432

(Continued)

FOREIGN PATENT DOCUMENTS

JP    2001-013063 A    1/2001
JP    2002-000586 A    1/2002

(Continued)

OTHER PUBLICATIONS

Aug. 8, 2017 International Search Report issued in International Patent Application No. PCT/JP2017/018655.

*Primary Examiner* — Eric F Winakur
(74) *Attorney, Agent, or Firm* — Oliff PLC

(57) ABSTRACT

A technique restrains degradation of a light emitting element. A biological information acquisition device acquires light receiving result by causing a light receiving unit to receive light emitted by a light emitting unit serving as a measurement-purpose light emitting unit, and acquires biological information by using the light receiving result. The light is emitted from the light emitting unit so as to acquire the light receiving result for one time, while a plurality of light emitting patterns are switched between a light emitting element which emits the light and a light emitting element which does not emit the light in a plurality of the light emitting elements.

12 Claims, 16 Drawing Sheets

(56) References Cited

U.S. PATENT DOCUMENTS

2012/0267615 A1  10/2012  Fujita et al.
2016/0098834 A1   4/2016  Eguchi et al.

FOREIGN PATENT DOCUMENTS

| JP | 2005-312887 A | 11/2005 |
| JP | 2009-233404 A | 10/2009 |
| JP | 2012-219078 A | 11/2012 |
| JP | 2014-124454 A |  7/2014 |
| JP | 2014-124455 A |  7/2014 |
| JP | 2014-235711 A | 12/2014 |
| JP | 2016-073483 A |  5/2016 |

\* cited by examiner

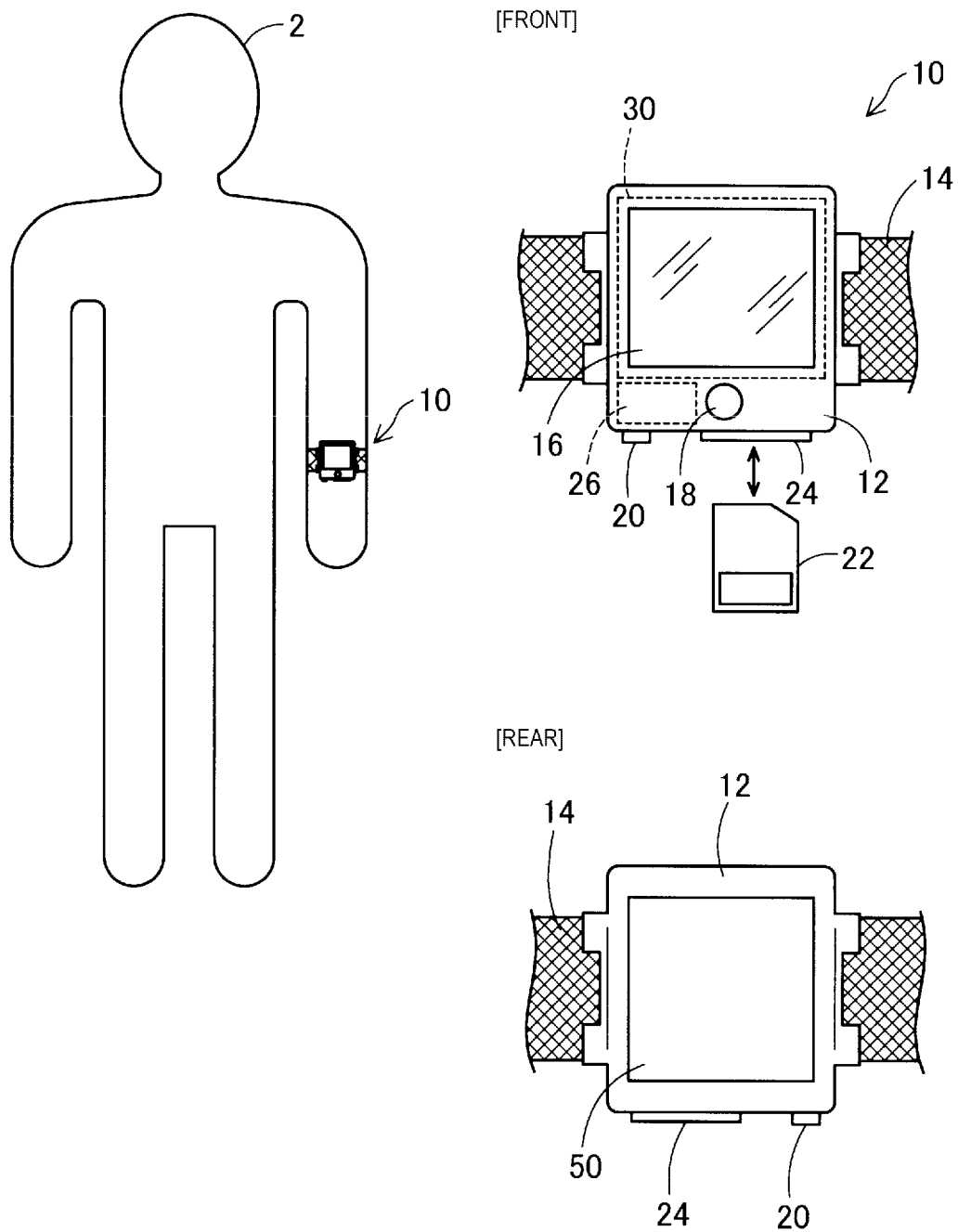
[Fig. 1]

[Fig. 2]
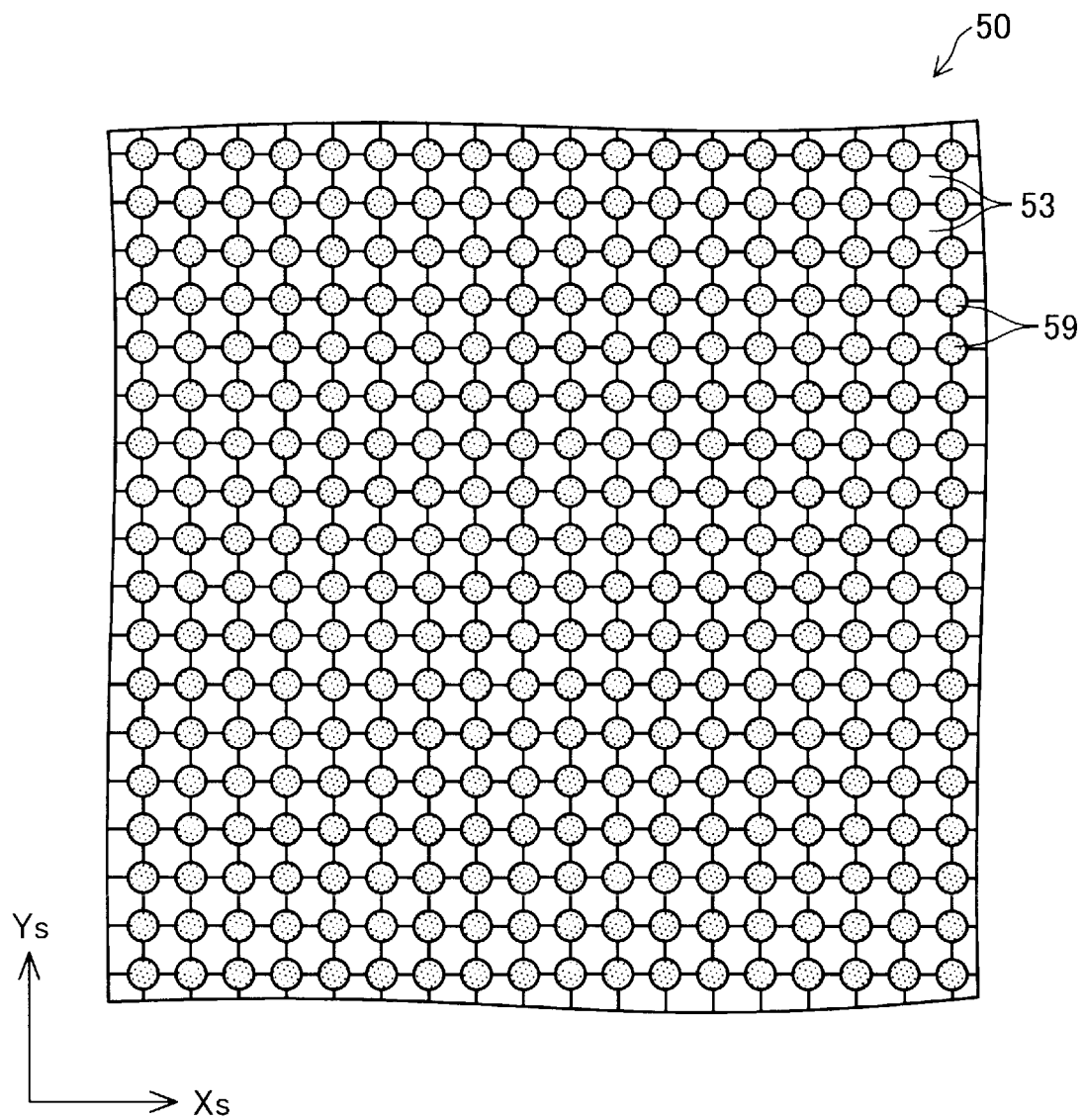

[Fig. 3]
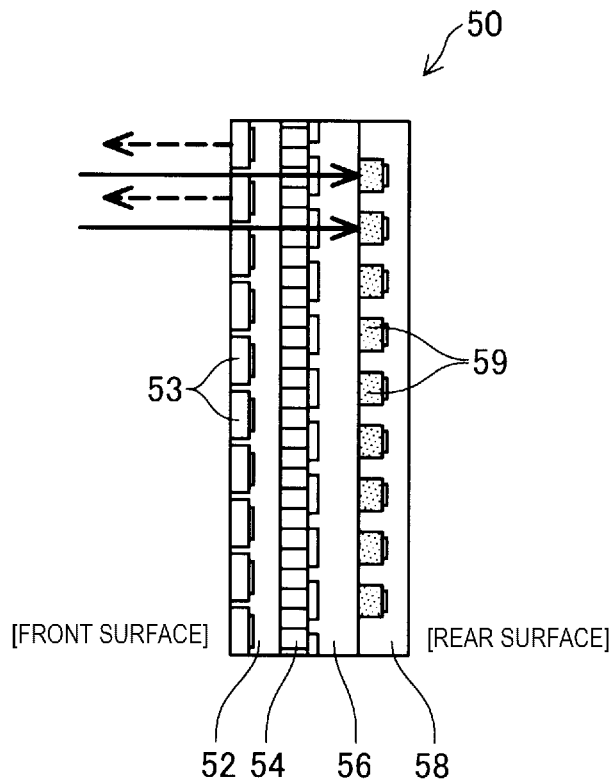
[Fig. 4]
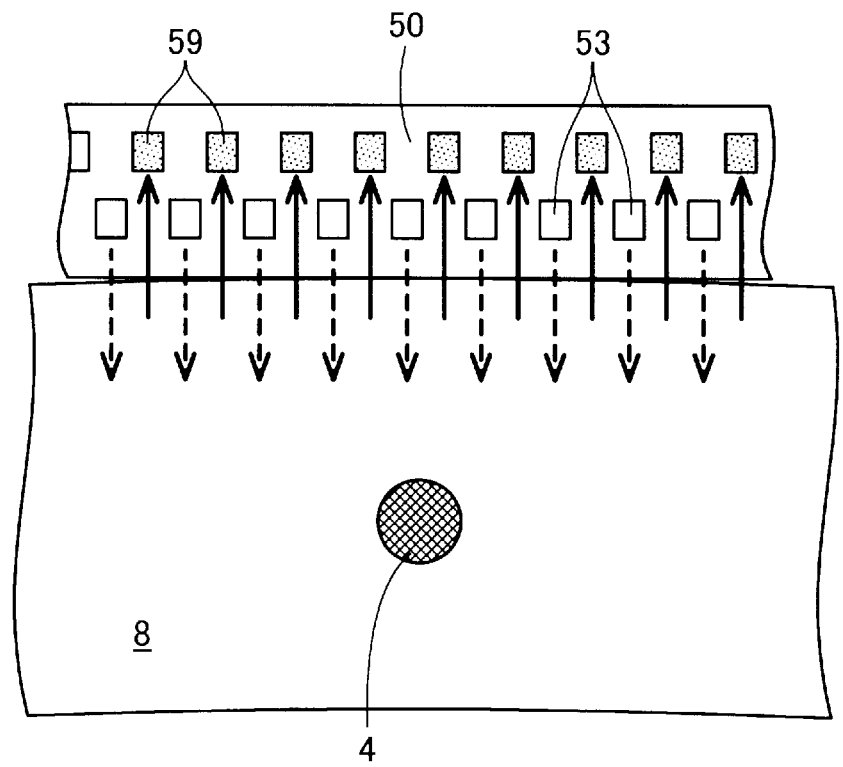

[Fig. 5]
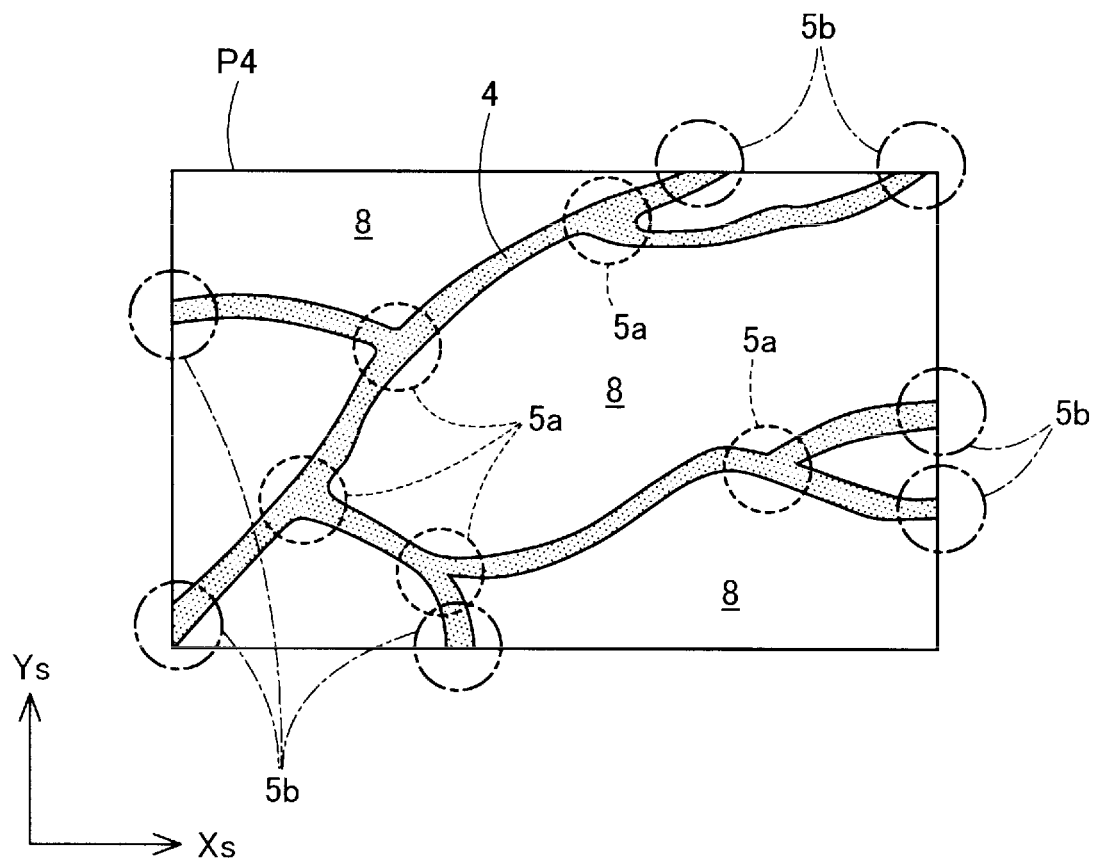
[Fig. 6]
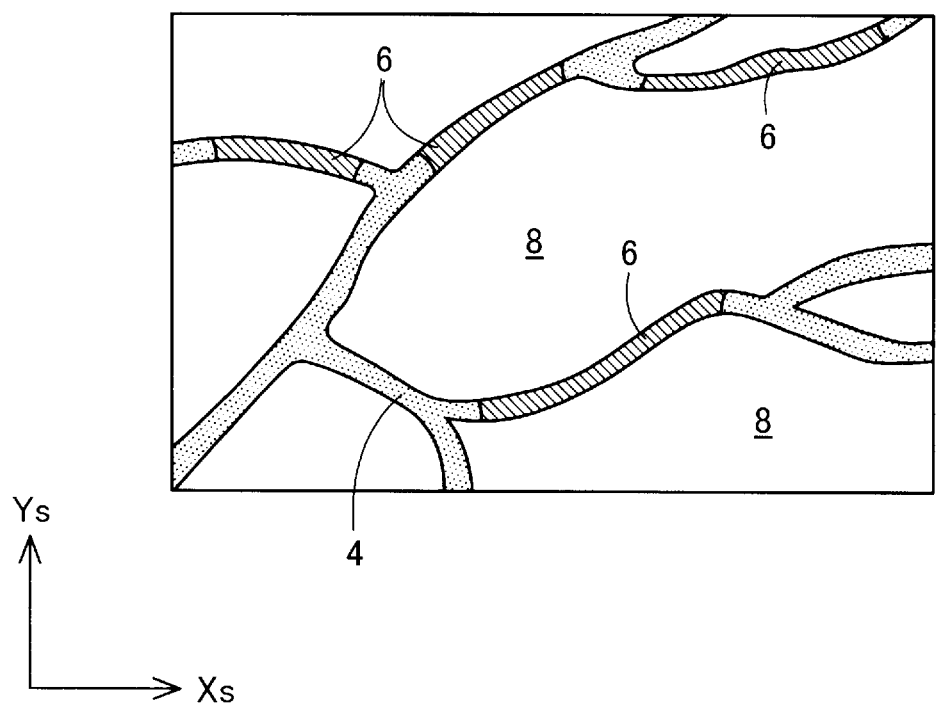

[Fig. 7]
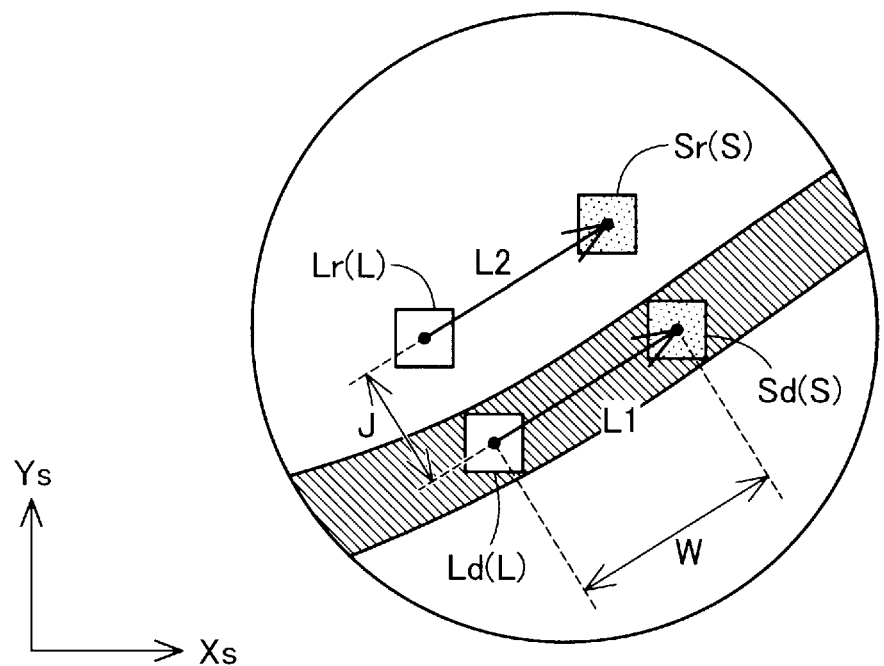
[Fig. 8]
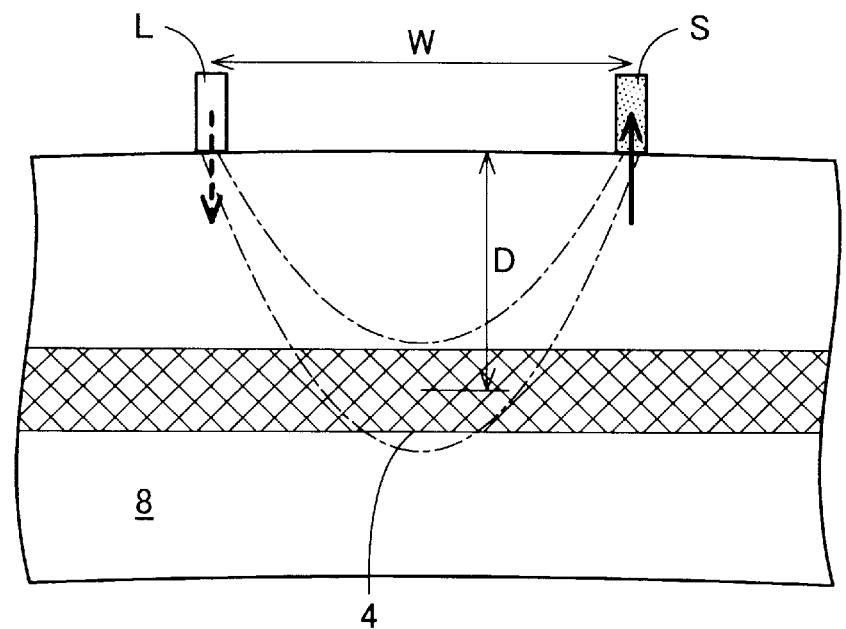

[Fig. 9]
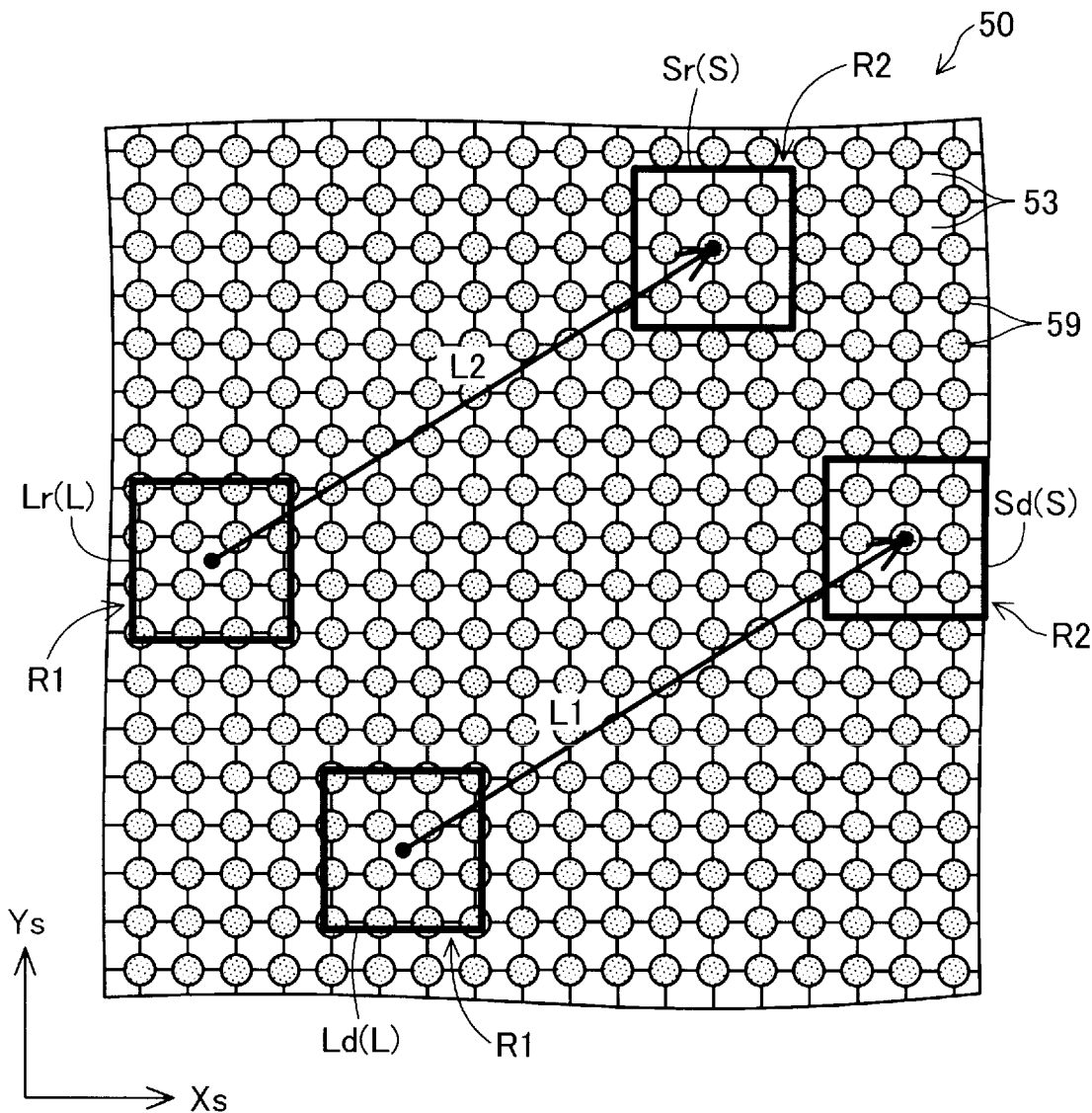

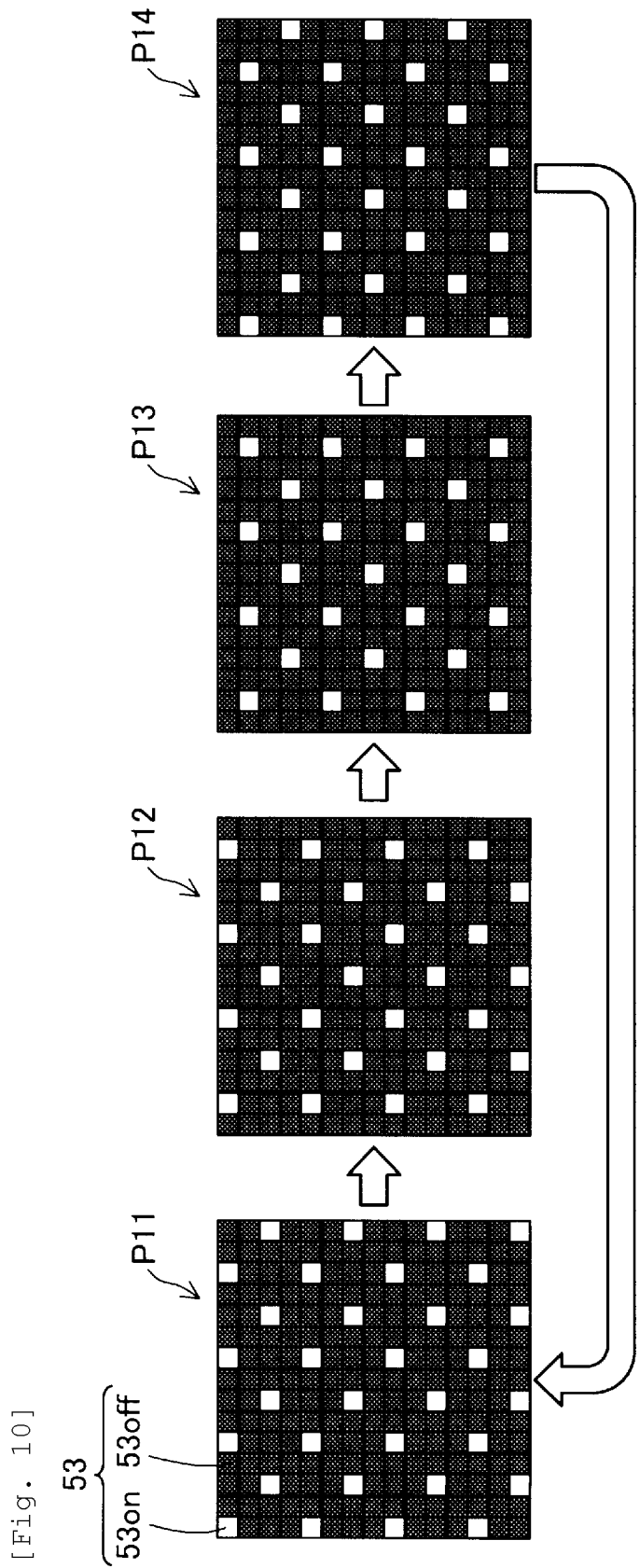

[Fig. 11]
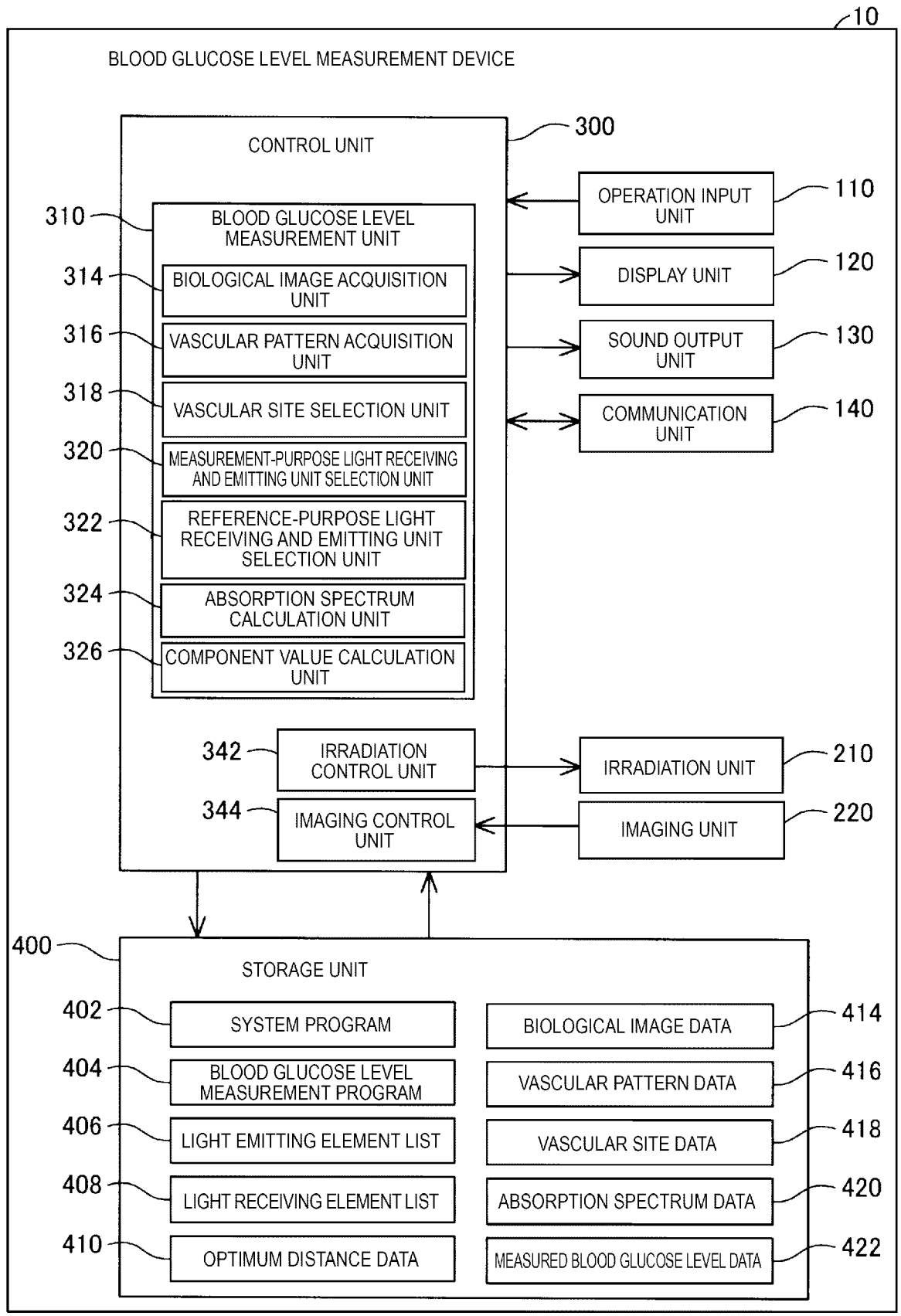

[Fig. 12]
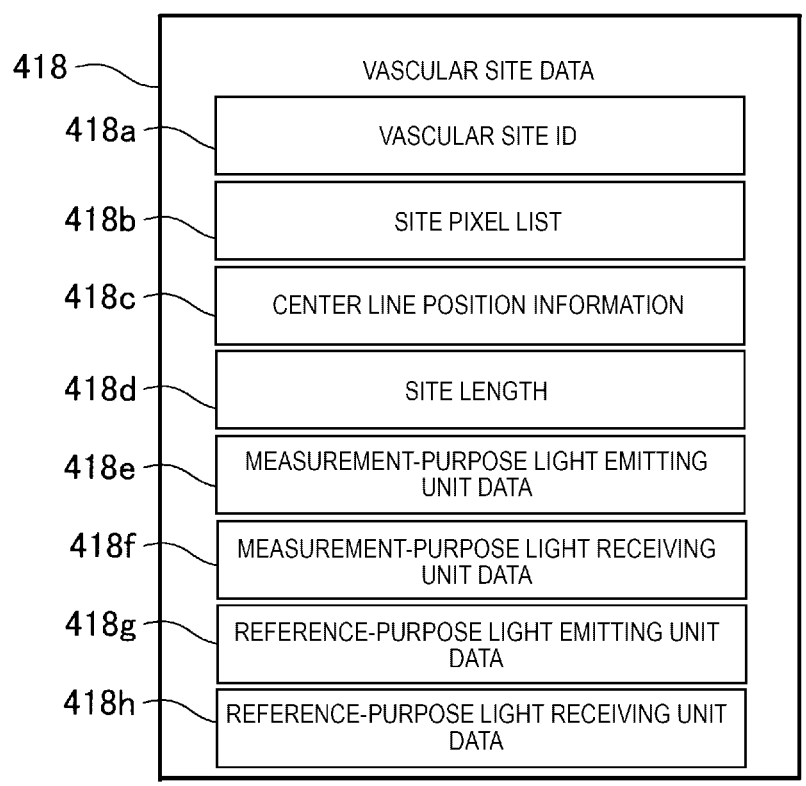

[Fig. 13]
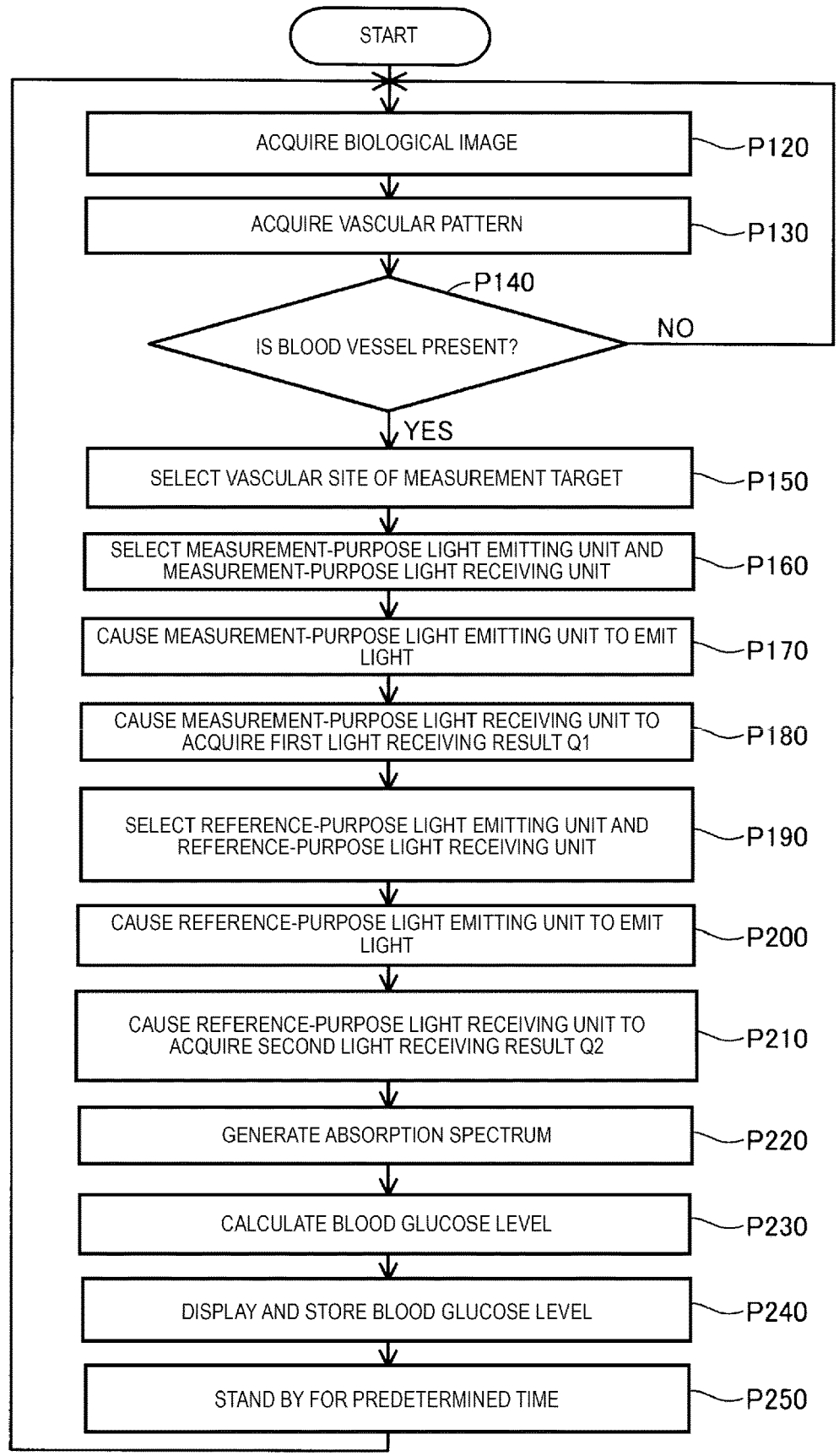

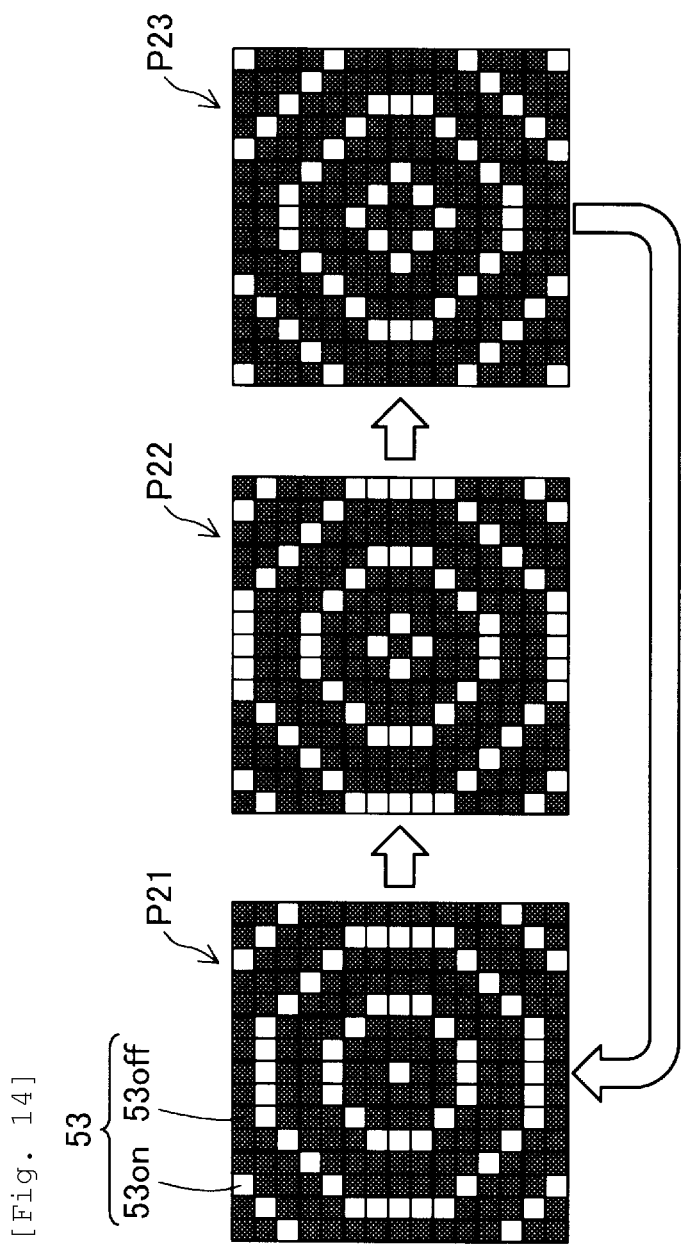

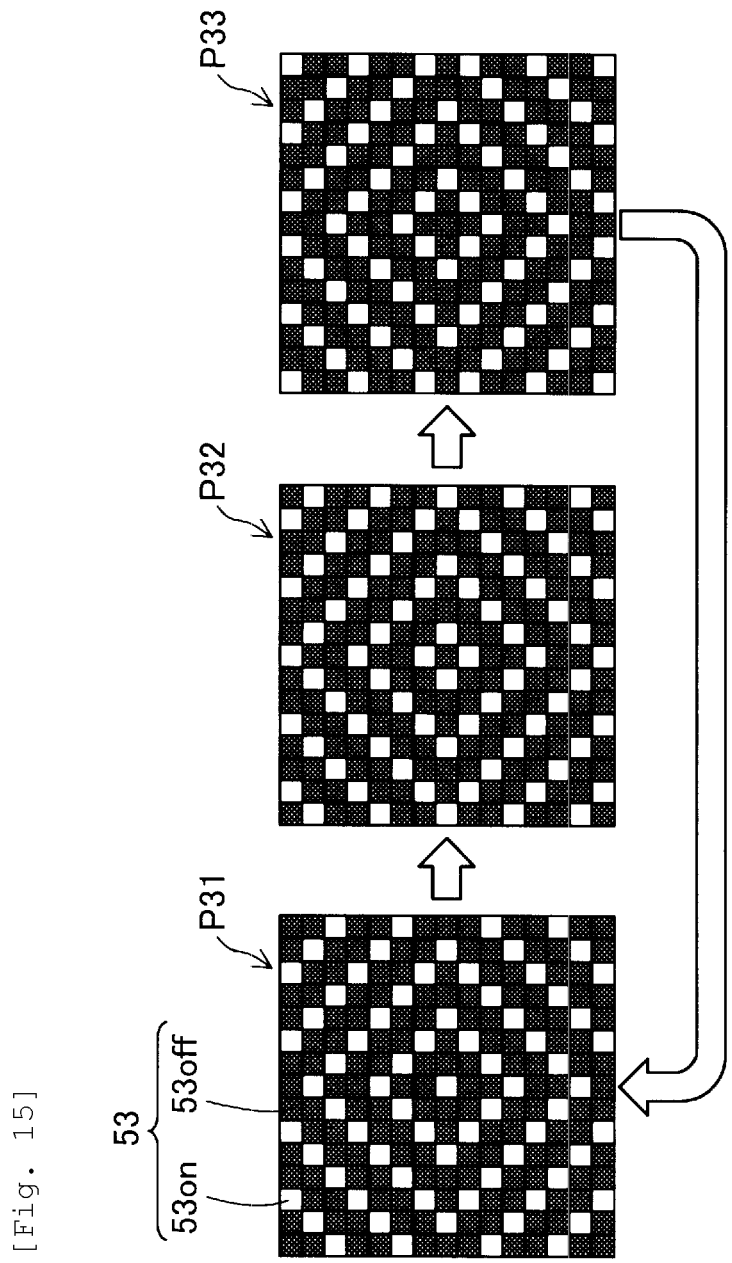

[Fig. 16]
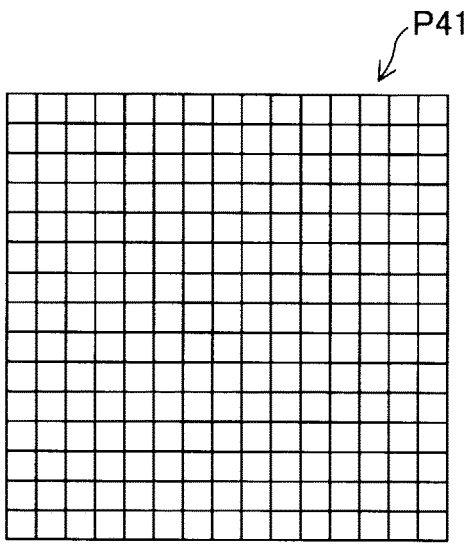
[Fig. 17]
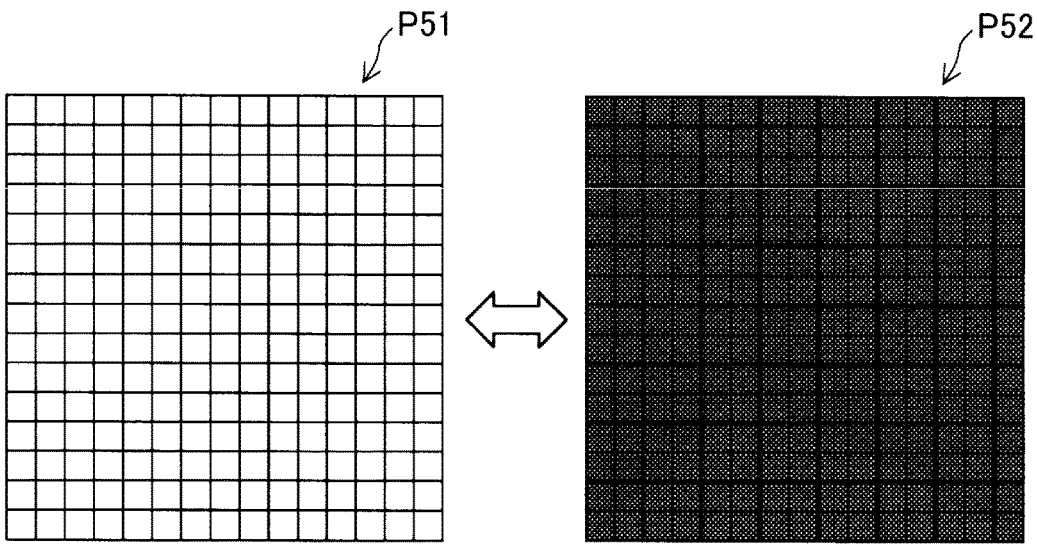
[Fig. 18]
| | LIGHTING PATTERN | LIGHT SOURCE LIFESPAN (LT80) [hr] |
|---|---|---|
| APPLICATION EXAMPLE 1 | PATTERN A (FIG. 10) | 1100 |
| APPLICATION EXAMPLE 2 | PATTERN B (FIG. 14) | 700 |
| APPLICATION EXAMPLE 3 | PATTERN C (FIG. 15) | 500 |
| COMPARATIVE EXAMPLE 1 | PATTERN D (FIG. 16) | 5 |
| COMPARATIVE EXAMPLE 2 | PATTERN E (FIG. 17) | 25 |

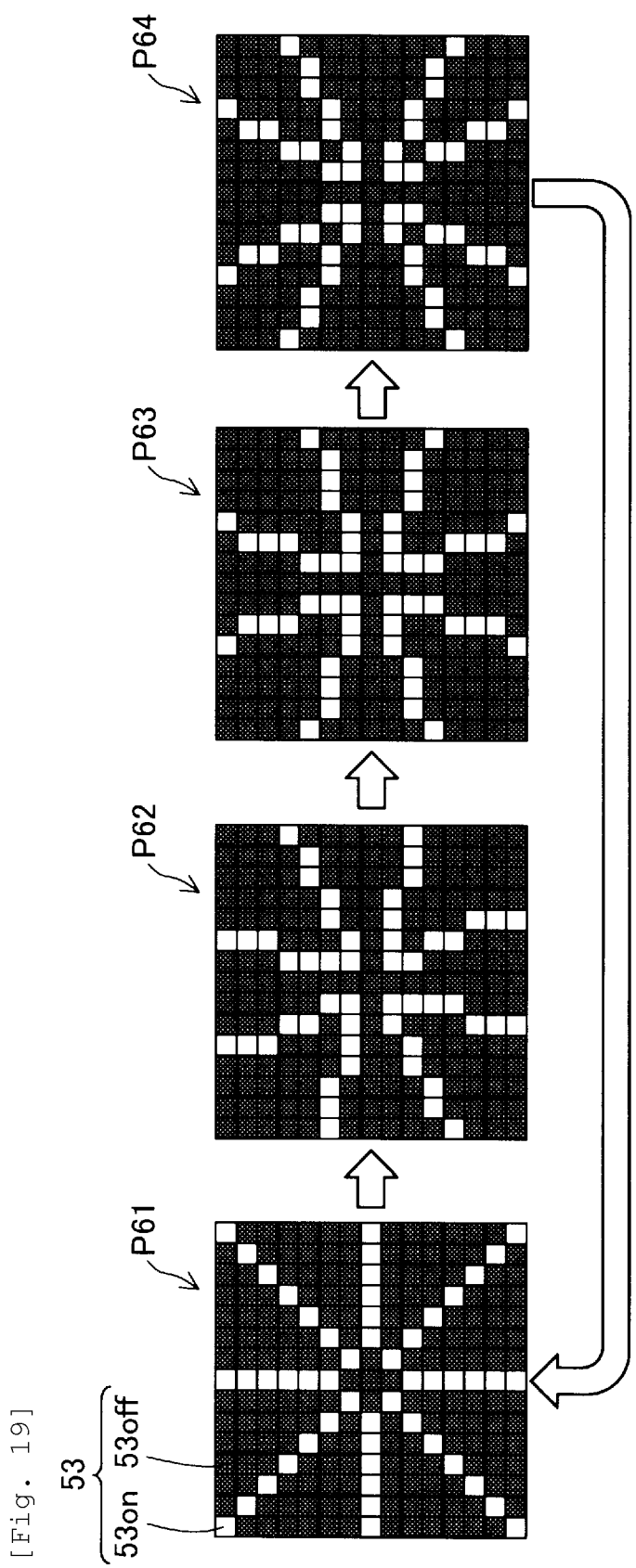

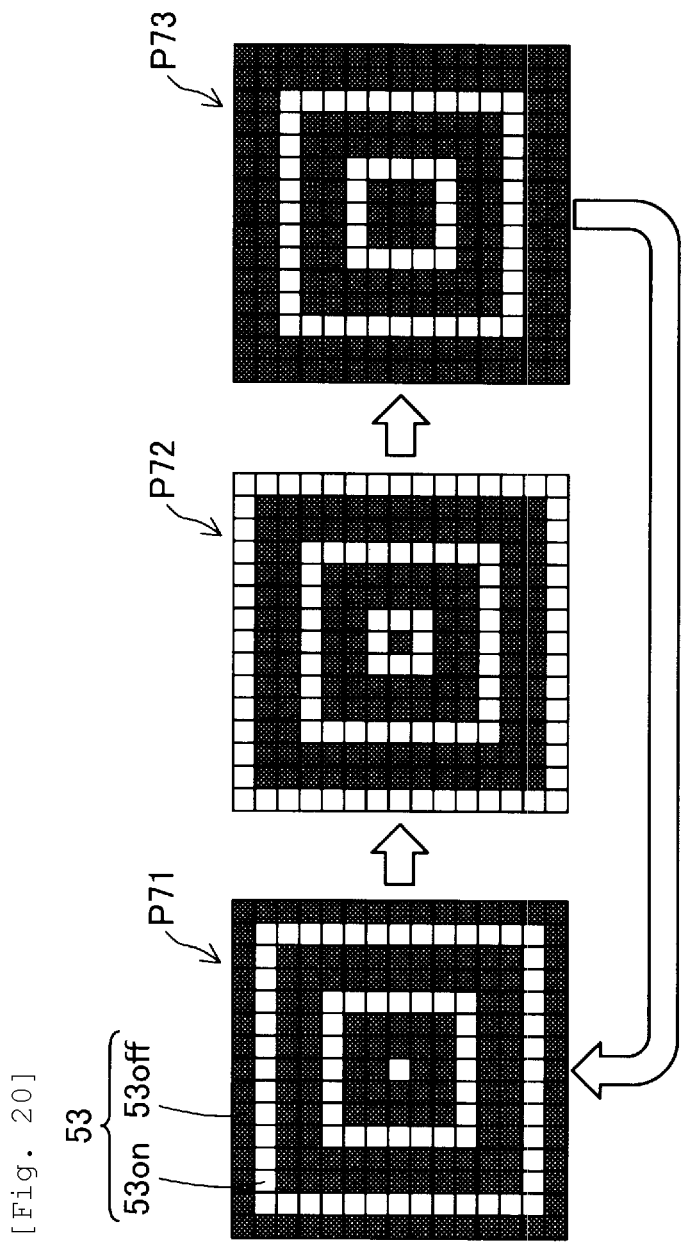

[Fig. 21]
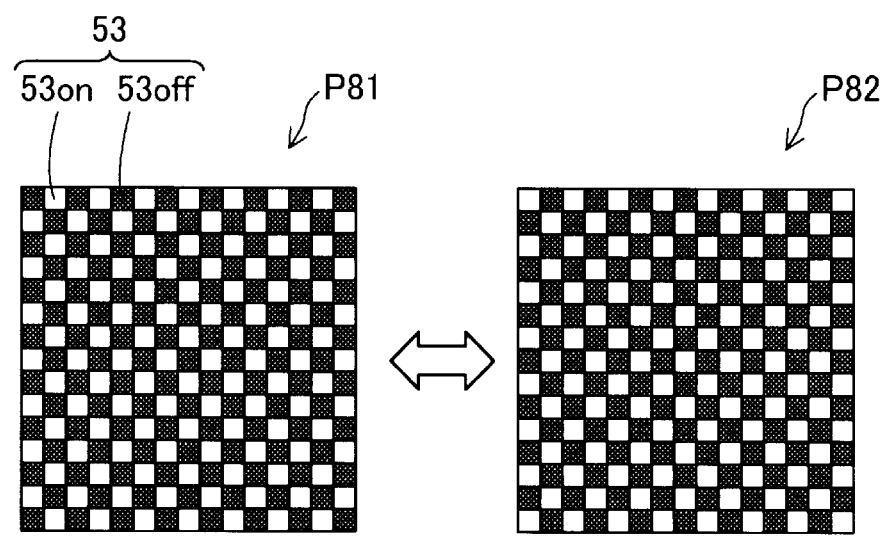

BIOLOGICAL INFORMATION ACQUISITION DEVICE AND BIOLOGICAL INFORMATION ACQUISITION METHOD

TECHNICAL FIELD

The present invention relates to a biological information acquisition device and a biological information acquisition method.

BACKGROUND ART

In the related art, a biological information acquisition device is known which acquires biological information relating to a blood vessel or blood in the blood vessel (for example, refer to PTL 1). PTL 1 discloses a technique for securing a light quantity by causing a plurality of light emitting elements to simultaneously emit light in order to measure a blood component in a living body.

CITATION LIST

Patent Literature

PTL 1: JP-A-2014-124455

SUMMARY OF INVENTION

Technical Problem

However, in a case where the plurality of light emitting elements are caused to simultaneously emit the light, the light emitting elements caused to emit the light generate heat, thereby causing a possibility that the light emitting elements may be degraded. In a case where the planarly arranged light emitting elements are caused to simultaneously emit the light, in the plurality of light emitting elements caused to emit the light, the light emitting element present in the vicinity of the center is particularly less likely to radiate the heat. This light emitting element tends to be degraded. Therefore, a technique for restraining the degradation of the light emitting element has been demanded.

Solution to Problem

The present invention is made in order to at least partially solve the above-described problem, and can be realized using the following aspects or application examples.

(1) According to a first aspect of the present invention, there is provided a biological information acquisition device. The biological information acquisition device includes a light emitting unit that is formed from a plurality of light emitting elements so as to emit light to a living body, a light receiving unit that receives the light transmitted through the living body, and a control unit that controls the light emitting unit and the light receiving unit. The control unit acquires a light receiving result by causing the light receiving unit to receive the light emitted from the light emitting unit, and acquires biological information by using the light receiving result. The light is emitted from the light emitting unit so as to acquire the light receiving result for one time, while a plurality of light emitting patterns are switched between the light emitting element which emits the light and the light emitting element which does not emit the light in the plurality of light emitting elements.

According to the biological information acquisition device in the present embodiment, the light is emitted from the light emitting unit so as to acquire the light receiving result for one time, while the plurality of light emitting patterns are switched between the light emitting element which emits the light and the light emitting element which does not emit the light in the plurality of light emitting elements. Accordingly, the light emitting element is restrained from continuously emitting the light. Therefore, it is possible to restrain the light emitting element from being degraded due to generated heat.

(2) The above-described biological information acquisition device may further include a plurality of the light emitting units. The control unit may specify a vascular position of the living body by causing at least one of the plurality of light emitting units to emit the light. Based on the vascular position, the light may be emitted from the light emitting unit in the plurality of light emitting units so as to acquire the light receiving result for the one time.

According to the biological information acquisition device in the present embodiment, based on the vascular position, the light is emitted from the light emitting unit so as to acquire the light receiving result for the one time. Accordingly, the light emitting unit suitable for acquiring the biological information relating to a blood vessel can be selected as a measurement-purpose light emitting unit. Therefore, it is possible to accurately acquire the biological information relating to the blood vessel.

(3) In the above-described biological information acquisition device, when the light is emitted from the light emitting unit so as to acquire the light receiving result for the one time, the respective light emitting patterns of the plurality of light emitting patterns may be all repeated the same number of times.

According to the biological information acquisition device in the present embodiment, the plurality of light emitting patterns are all repeated the same number of times. In this manner, it is possible to reduce a deviation of a light emitting position of the light emitting element in the respective light emitting patterns. Therefore, it is possible to accurately acquire the biological information relating to the blood vessel.

(4) In the above-described biological information acquisition device, the light emitting elements emitting the light in the respective light emitting patterns of the plurality of light emitting patterns may be located at positions which are point-symmetric with respect to a center of the light emitting unit or which are line-symmetric with respect to a line passing through the center.

According to the biological information acquisition device in the present embodiment, it is possible to restrain variations in a light quantity between the light emitting patterns. As a result, it is possible to accurately acquire the biological information relating to the blood vessel.

(5) In the above-described biological information acquisition device, in the respective light emitting patterns of the plurality of light emitting patterns, the light emitting element which does not emit the light may be present in the light emitting elements adjacent to the light emitting element which emits the light.

According to the biological information acquisition device in the present embodiment, the heat generated by the light emitting element which emits the light is diffused in a direction having the light emitting element which does not emit the light while being adjacently present. Therefore, it is possible to restrain the light emitting element from being degraded due to generated heat.

(6) In the above-described biological information acquisition device, in the plurality of light emitting patterns, the light emitting element which emits the light in an optional light emitting pattern may not emit the light in the light emitting pattern subsequent to the optional light emitting pattern.

According to the biological information acquisition device in the present embodiment, it is possible to restrain the light emitting element from being degraded due to generated heat.

(7) In the above-described biological information acquisition device, the light emitting unit may emit the light including a near infrared ray having a wavelength of 0.7 μm to 2.5 μm.

According to the biological information acquisition device in the present embodiment, the biological information can be acquired using the near infrared ray which is likely to be transmitted through the living body.

(8) In the above-described biological information acquisition device, in the plurality of light emitting patterns, the light emitting elements, the number of which is a predetermined number or more, may emit the light.

Compared to a case where the light emitting elements, the number of which is smaller than the predetermined number, are caused to emit the light, the biological information acquisition device according to the present embodiment can obtain sufficient light emitting intensity.

(9) In the above-described biological information acquisition device, the biological information may include glucose concentration in blood of the living body.

According to the biological information acquisition device in the present embodiment, it is possible to acquire the glucose concentration in the blood of the living body.

(10) In the above-described biological information acquisition device, the biological information may include oxygen saturation in blood of the living body.

According to the biological information acquisition device in the present embodiment, it is possible to acquire the oxygen saturation in the blood of the living body.

(11) In the above-described biological information acquisition device, an OLED may be used as the light emitting element.

According to the biological information acquisition device in the present embodiment, the OLED can be used.

The present invention can also be realized using various aspects other than the above-described aspects. For example, the present invention can be realized using aspects such as a biological information acquisition method of acquiring biological information by using a biological information acquisition device including a light emitting unit that is formed from a plurality of light emitting elements so as to emit light to a living body, and a light receiving unit that receives the light transmitted through the living body, and a computer program for realizing this method, and a non-transitory recording medium (non-transitory storage medium) for storing the computer program.

BRIEF DESCRIPTION OF DRAWINGS

FIG. 1 is a schematic view illustrating a configuration of a biological information acquisition device according to a first embodiment.
FIG. 2 is a schematic plan view illustrating a portion of a sensor module.
FIG. 3 is a configuration diagram of the sensor module.
FIG. 4 is a schematic view for describing a state of acquiring a vascular pattern (vascular position).
FIG. 5 is a view illustrating an example of a vascular pattern obtained based on a biological image.
FIG. 6 illustrates an example of a vascular site of a measurement target obtained based on the vascular pattern in FIG. 5.
FIG. 7 is a view for describing selection of a light emitting unit and a light receiving unit.
FIG. 8 is a view for describing the light propagation inside a biological tissue.
FIG. 9 is a schematic view illustrating a relationship between the light emitting unit and a light emitting element and a relationship between the light receiving unit and a light receiving element.
FIG. 10 is a schematic view illustrating a plurality of light emitting patterns according to the present embodiment.
FIG. 11 is a functional configuration diagram of a blood glucose level measurement device according to the present embodiment.
FIG. 12 is a view illustrating an example of data configuration of vascular site data.
FIG. 13 is a flowchart for describing a flow in a blood glucose level measurement process.
FIG. 14 is a schematic view illustrating a light emitting pattern which is different from that according to the present embodiment.
FIG. 15 is a schematic view illustrating a light emitting pattern which is different from that according to the present embodiment.
FIG. 16 is a schematic view illustrating a lighting pattern according to a comparative example.
FIG. 17 is a schematic view illustrating a lighting pattern according to a comparative example.
FIG. 18 illustrates a result obtained by measuring a light source lifespan.
FIG. 19 is a schematic view illustrating a light emitting pattern which is different from that according to the present embodiment.
FIG. 20 is a schematic view illustrating a light emitting pattern which is different from that according to the present embodiment.
FIG. 21 is a schematic view illustrating a light emitting pattern which is different from that according to the present embodiment.

DESCRIPTION OF EMBODIMENTS

A. First Embodiment

A1. Device Configuration

FIG. 1 is a schematic view illustrating a configuration of a biological information acquisition device 10 according to a first embodiment. The biological information acquisition device 10 is a biological information acquisition device for noninvasively measuring biological information of a user 2 by using light. In the present embodiment, as the biological information, the biological information acquisition device 10 acquires a blood glucose level which is glucose concentration in blood of the user 2. The biological information acquisition device 10 is also called a blood glucose level measurement device 10. The biological information acquisition device 10 is a wristwatch type, and is a wearable device (wearable instrument) configured to include a main body case 12 and a fixing band 14 for fixing and wearing the main body case 12 to and on a wrist or an arm of the user 2.

A touch panel 16 or an operation switch 18 is disposed on a front surface (surface facing outward when worn by the user 2) of the main body case 12. The touch panel 16 or the operation switch 18 is used so that the user 2 can input a measurement start instruction thereto or a measurement result can be displayed on the touch panel 16.

In addition, a communication device 20 for communicating with an external device and a reader/writer 24 of a memory card 22 are disposed on a side surface of the main body case 12. The communication device 20 is realized by a jack for attaching and detaching a wired cable, or by a wireless communication module and an antenna for wireless communication. The memory card 22 is a data rewritable nonvolatile memory such as a flash memory, a ferroelectric random access memory (FeRAM), and a magnetoresistive random access memory (MRAM).

In addition, a sensor module 50 is disposed on a rear surface of the main body case 12 so that the sensor module 50 can be in contact with a skin surface of the user 2. The sensor module 50 is a measurement-purpose device which emits measurement light onto a skin surface of the user 2 and receives the light transmitted through or reflected on a body of the user 2, and is a thin type image sensor internally equipped with a light source.

Furthermore, the main body case 12 is internally equipped with a rechargeable battery 26 and a control board 30. As a method for charging the battery 26, a configuration may be adopted in which an electrical contact is disposed on the rear surface side of the main body case 12 and the battery 26 is set in a cradle connected to a domestic power source so as to be charged via the electrical contact by way of the cradle. Alternatively, wireless charging may be employed.

The control board 30 is provided with a central processing unit (CPU), a main memory, a memory for measurement data, a touch panel controller, and a sensor module controller. The main memory is a storage medium which can store a program and initial set data or which can store computed values of the CPU. The main memory is realized by a RAM, a read only memory (ROM), and a flash memory. A configuration may be adopted in which the program and the initial set data are stored in the memory card 22. The memory for measurement data is a storage medium for storing the measurement data, and is realized by a data rewritable nonvolatile memory such as a flash memory, a ferroelectric memory (FeRAM), and a magnetoresistive memory (MRAM). A configuration may be adopted in which the measurement data is stored in the memory card 22.

FIGS. 2 and 3 are configuration diagrams of the sensor module 50. FIG. 2 is a schematic plan view illustrating a portion of the sensor module 50, and FIG. 3 is a schematic sectional view of the sensor module 50. As illustrated in FIG. 2, the sensor module 50 has a plurality of light emitting elements 53 and a plurality of light receiving elements 59 which are respectively and regularly arranged inside a light receiving and emitting region. Here, the light receiving and emitting region includes the plurality of light emitting elements 53 and the plurality of light receiving elements 59.

As illustrated in FIG. 3, the sensor module 50 is an optical sensor configured so that a light emitting layer 52 in which the plurality of light emitting elements 53 are two-dimensionally arranged in a planar fashion, a light blocking layer 54 which selectively blocks the light other than the light directed toward a light receiving layer 58, a spectral layer 56 which selectively transmits near infrared rays, and the light receiving layer 58 in which the plurality of the light receiving elements 59 are two-dimensionally arranged in a planar fashion are stacked one on another. The sensor module 50 is disposed on the rear surface side of the main body case 12 so that the front surface side (surface on the light emitting layer 52 side) faces the skin surface of the user 2.

The light emitting element 53 emits the light to the living body. For example, the light emitting element 53 is realized by a light emitting diode (LED) or an organic light emitting diode (OLED). In the present embodiment, in order to measure a blood glucose level (glucose concentration in the blood), the light emitting element 53 can emit the light including near infrared rays (light having a wavelength of 0.7 μm to 2.5 μm) having subcutaneously transmittance capability. In the present embodiment, the OLED is used as the light emitting element 53.

The light receiving element 59 receives the light transmitted through or reflected on the living body, and outputs an electric signal corresponding to the received light quantity. For example, the light receiving element 59 is realized by an imaging element such as a charge coupled device (CCD) image sensor and a complementary metal oxide semiconductor (CMOS) image sensor. One light receiving element 59 includes a plurality of elements for receiving each wavelength component necessary for calibration.

As illustrated in FIG. 2, the light emitting element 53 and the light receiving element 59 are arranged in a matrix on a plane defined by a common Xs-Ys orthogonal coordinate system. The light emitting element 53 and the light receiving element 59 respectively have the same arrangement interval in Xs and Ys axis directions. However, both of these are arranged so as to be alternate on an Xs-Ys plane. That is, both of these are arranged so that positions of the light emitting element 53 and the light receiving element 59 in the Xs and Ys axis directions are shifted from each other by a predetermined length.

Each arrangement interval between the light emitting element 53 and the light receiving element 59 can be appropriately set. For example, it is preferable to set the arrangement interval to 1 μm to 500 μm. In view of a balance between manufacturing cost and measurement accuracy, the arrangement interval can be set to 50 μm to 200 μm, for example. The light emitting element 53 and the light receiving element 59 may be juxtaposed with each other without being limited to a configuration in which the light emitting element 53 and the light receiving element 59 are stacked on each other.

A2. Measurement Principle

(A) Measurement of Blood Glucose Level

A measurement principle of the blood glucose level according to the present embodiment will be described. In order to measure the blood glucose level, the blood glucose level measurement device 10 is fixed to the user 2 with the fixing band 14 so that the sensor module 50 is in close contact with the skin surface of the user 2. Since the sensor module 50 is in close contact with the skin surface, it is possible to restrain factors that lower the measurement accuracy, such as reflection of the measurement light on the skin surface and scattering near the skin surface. Then, the blood vessel inside the biological tissue directly below the sensor module 50 is set as a measurement target. The measurement light is transmitted through the blood vessel, and the light including the transmitted light passing through the blood vessel is received so as to obtain an absorption spectrum. In this manner, the blood glucose level is estimated and calculated.

(A-1) Acquisition of Vascular Pattern

Specifically, first, a vascular pattern (vascular position) viewed from the skin surface is acquired. The acquisition of the vascular pattern can be realized in the same way as vein position detection in the known vein authentication technology.

FIG. 4 is a schematic view for describing a state of acquiring the vascular pattern (vascular position). As illustrated in FIG. 4, all of the light emitting elements 53 of the sensor module 50 are caused to simultaneously emit the light so as to irradiate the skin surface of the user 2 with the measurement light. Then, the light receiving element 59 is used, and the light in which the measurement light is transmitted through the biological tissue (transmitted light) or the light reflected on the biological tissue (reflected light) is received, that is, imaged, thereby acquiring a biological image. When the biological image is acquired, only some of the light emitting elements 53 of the sensor module 50 may be caused to emit the light.

The blood vessel is more likely to absorb near infrared rays compared to a non-blood vessel portion. Thus, in the acquired biological image, the blood vessel portion has lower luminance, and is darker than the non-blood vessel portion. Therefore, a portion having the lower luminance is extracted from the biological image. In this manner, the vascular pattern can be extracted. That is, it is determined whether or not the luminance of each pixel configuring the biological image is equal to or smaller than a predetermined threshold. In this manner, it is possible to determine whether or not the blood vessel exists directly below the corresponding light receiving element 59, that is, it is possible to acquire the vascular position.

FIG. 5 is a view illustrating an example of a vascular pattern P4 obtained based on the biological image. The vascular pattern P4 is information indicating whether a portion is the blood vessel or a non-vascular site for each pixel configuring the biological image, that is, for each position of the light receiving elements 59. In FIG. 5, a hatched band-like portion is a blood vessel 4, and other white outlined portions are extracted as a non-vascular site 8.

(A-2) Selection of Vascular Site as Measurement Target

If the vascular pattern is acquired, the blood vessel (more specifically, the vascular site) serving as a measurement target is subsequently selected. The vascular site serving as the measurement target is selected so as to satisfy the following selection condition. The selection condition is that "the vascular site is a bifurcated portion or joined portion of the blood vessel and a portion other than an image end portion, and that the vascular site has a predetermined length and a predetermined width in a longitudinal direction of the blood vessel".

There is a possibility that the light passing through the blood vessel other than the measurement target may be mixed with the received light in a bifurcated/joined site 5a (refer to FIG. 5) of the blood vessel. The light transmitted through the blood vessel other than the vascular site serving as the measurement target affects an absorption spectrum of the vascular site serving as the measurement target, thereby causing a possibility that measurement accuracy may become poor. Therefore, the vascular site serving as the measurement target is selected from a portion of the blood vessel other than the bifurcated/joined site 5a of the blood vessel.

In an image end portion 5b (refer to FIG. 5) of the living body, a bifurcated or joined structure of the blood vessel in the vicinity of the outside of the image is unknown. Accordingly, there is a possibility that the measurement accuracy may become poor due to the same reason as described above. In order to avoid this possibility, the vascular site serving as the measurement target is selected from the portion of the blood vessel other than the image end portion 5b.

The light emitted from the light emitting element 53 is diffused and reflected inside the biological tissue, and the light is partially received by the light receiving element 59. In other words, the light partially received by the light receiving element 59 becomes the light transmitted through the blood vessel serving as the measurement target. As a proportion of the transmitted light becomes higher, the transmitted light can become an absorption spectrum which more remarkably shows the characteristics of the components contained in the blood of the blood vessel serving as the measurement target. That is, the measurement accuracy is improved.

The blood vessel which is relatively thinly imaged (short blood vessel in the width direction) is the blood vessel which is inherently thin, or is the blood vessel which is located at a relatively deep position. In this blood vessel, the light quantity of the transmitted light decreases, and the measurement accuracy may become poor. Therefore, the vascular site serving as the measurement target is selected from the portion of the blood vessel (that is, a vascular site having a predetermined width) excluding the blood vessel which is thinly imaged.

FIG. 6 is an example of a vascular site 6 serving as the measurement target obtained based on the vascular pattern P4 in FIG. 5. In FIG. 6, an obliquely hatched portion of the blood vessel 4 is the vascular site 6 selected as the measurement target.

(A-3) Selection of Light Emitting Unit and Light Receiving Unit

Subsequently, a light emitting unit L and a light receiving unit S are selected.

FIG. 7 is a view for describing selection between the light emitting unit L and the light receiving unit S. The light emitting unit L and the light receiving unit S are selected based on the vascular position. In the present embodiment, (i) the light emitting unit L located above the blood vessel is selected as a measurement-purpose light emitting unit Ld, and (ii) the light receiving unit S separated from the measurement-purpose light emitting unit Ld by a predetermined distance W and located above the blood vessel is selected as a measurement-purpose light receiving unit Sd. Here, the term of "above the blood vessel" means that these are located above the vascular site 6 serving as the measurement target.

In addition, (iii) the light emitting unit L which is not located above the blood vessel is selected as a reference-purpose light emitting unit Lr, and (iv) the light receiving unit S which is separated from the reference-purpose light emitting unit Lr by the predetermined distance W and is not located above the blood vessel is selected as a reference-purpose light receiving unit Sr. Here, the term of "not located above the blood vessel" means that these are not located above the blood vessel 4 including the vascular site serving as the measurement target. The predetermined distance W is determined as follows.

FIG. 8 is a view for describing light propagation inside the biological tissue, and illustrates a sectional view taken along the depth direction. The light emitted from one of the light emitting units L is diffused and reflected inside the biological tissue, and the emitted light partially reaches the light receiving unit S. A propagation path of the light forms a so-called banana shape (region interposed between two arcs). The width in the depth direction is most widened in the vicinity of substantially the center, and the entire depth (reachable depth) is deepened in accordance with an interval between the light emitting element 53 and the light receiving element 59.

In order to improve the measurement accuracy, it is desirable that the more light transmitted through the blood vessel 4 is received by the light receiving unit S. From this viewpoint, it is preferable that the blood vessel 4 serving as the target is located below the light emitting unit L and the light receiving unit S. The predetermined distance W is determined in accordance with an assumed depth D of the blood vessel 4 serving as the target. The predetermined distance W, that is, the optimum interval W between the light emitting unit L and the light receiving unit S represents a distance approximately twice the depth D from the skin surface of the blood vessel 4. For example, if the depth D is approximately 3 mm, the optimum distance W is approximately 5 to 6 mm. Next, a relationship between the light emitting unit L and the light emitting element 53, and a relationship between the light receiving unit S and the light receiving element 59 will be described.

FIG. 9 is a schematic view illustrating the relationship between the light emitting unit L and the light emitting element 53, and the relationship between the light receiving unit S and the light receiving element 59. The light emitting unit L according to the present embodiment is formed from a plurality of the light emitting elements 53 inside a light emitting region R1. The light emitting region R1 is a partial region in a light receiving and emitting region of the sensor module 50, and indicates a region having a prescribed shape and size. In FIG. 9, the light emitting region R1 is a region where three light emitting elements 53 are provided in a vertical direction (Ys-direction) and three light emitting elements 53 are provided in a horizontal direction (Xs-direction).

In the present embodiment, the sensor module 50 includes the light emitting elements 53, the number of which is more than the number of the light emitting elements 53 included inside the light emitting region R1. Therefore, the plurality of light emitting units L are present in the light receiving and emitting region of the sensor module 50. Then, a measurement-purpose light emitting unit Ld or a reference-purpose light emitting unit Lr is selected from the plurality of light emitting units L. A region including the plurality of light emitting elements 53 which are caused to emit the light as the measurement-purpose light emitting unit Ld will be referred to as a first light emitting region, and a region including the plurality of light emitting elements 53 which are caused to emit the light as the reference-purpose light emitting unit Lr will be referred to as a second light emitting region.

Similarly, the light receiving unit S in the present embodiment is formed to include the plurality of light receiving elements 59 inside a light receiving region R2. The light receiving region R2 is a partial region of the light receiving and emitting region of the sensor module 50, and means a region having a prescribed shape and size. In FIG. 9, in the light receiving region R2, the three light receiving elements 59 are provided in the vertical direction (Ys-direction), and the three light receiving elements 59 are provided in the horizontal direction (Xs-direction). In this manner, all of the light receiving elements 59 inside the light receiving region R2 are set to receive the light as the light receiving unit S.

In the present embodiment, the sensor module 50 includes the light receiving elements 59, the number of which is more than the number of light receiving elements 59 included in the light receiving region R2. Therefore, the plurality of light receiving units S are present in the light receiving and emitting region of the sensor module 50. Then, a measurement-purpose light receiving unit Sd or a reference-purpose light receiving unit Sr is selected from the plurality of light receiving units S. A region including the plurality of light receiving elements 59 which are caused to receive the light as the measurement-purpose light receiving unit Sd will be referred to as a first light receiving region, and a region including the plurality of light receiving elements 59 which are caused to receive the light as the reference-purpose light receiving unit Sr will be referred to as a second light receiving region.

All of the light receiving elements 59 inside the light receiving region R2 may not be caused to receive the light. In the present embodiment, the predetermined distance W between the light emitting unit L and the light receiving unit S means a distance between a centroid of the light emitting region R1 and a centroid of the light receiving region R2. These centroids are geometric centroids determined depending on a shape of the region.

In the present embodiment, a straight line L1 connecting the measurement-purpose light emitting unit Ld and the measurement-purpose light receiving unit Sd to each other and a straight line L2 connecting the reference-purpose light emitting unit Lr and the reference-purpose light receiving unit Sr are substantially parallel to each other. The term of "substantially parallel" means that an angle formed between the two straight lines L1 and L2 falls within 10°. In addition, it is preferable that a distance J between the measurement-purpose light emitting unit Ld and the reference-purpose light emitting unit Lr is 6 mm or shorter. In the present embodiment, the distance J is set to 5 mm.

(A-4) Measurement

If the measurement-purpose light emitting unit Ld, the measurement-purpose light receiving unit Sd, the reference-purpose light emitting unit Lr, and the reference-purpose light receiving unit Sr are selected for the vascular site 6 serving as the measurement target, the blood glucose level information is acquired. Specifically, first, the measurement-purpose light emitting unit Ld is caused to emit the light so as to acquire a light receiving result Q1 (referred to as a "first light receiving result Q1") of the light from the measurement-purpose light receiving unit Sd. Next, the reference-purpose light emitting unit Lr is caused to emit the light so as to acquire a light receiving result Q2 (referred to as a "second light receiving result Q2") of the light from the reference-purpose light receiving unit Sr. Then, an absorption spectrum is generated using the light receiving result Q1 and the light receiving result Q2.

In this case, for example, a wavelength of the light to be emitted is changed by the light emitting unit L. In this manner, a wavelength $\lambda$ of the light emitted to the skin surface is changed within a near infrared region, and transmittance of the vascular site 6 is obtained for each wavelength $\lambda$. The transmittance $T(\lambda)$ is obtained as $T(\lambda)=Os(\lambda)/Or(\lambda)$, based on light intensity $Os(\lambda)$ obtained by the measurement-purpose light receiving unit Sd and light intensity $Or(\lambda)$ obtained by the reference-purpose light receiving unit Sr. Then, absorbance is obtained from the transmittance so as to generate the absorption spectrum.

Here, a calculation principle of the transmittance will be briefly described. In general, if the intensity of the light emitted by the light emitting unit L is set to $P(\lambda)$, the transmittance of an object portion through which the emitted light is transmitted is set to $T(\lambda)$, and sensitivity determined in the light receiving unit S is set to $S(\lambda)$, the light intensity $O(\lambda)$ obtained by the light receiving unit S is expressed by $O(\lambda)=P(\lambda) \cdot T(\lambda) \cdot S(\lambda)$.

Based on this relational expression, the light intensity $Or(\lambda)$ obtained by the reference-purpose light receiving unit Sr which does not include the transmitted light of the blood vessel 4 is obtained as $Or(\lambda)=P(\lambda) \cdot S(\lambda)$, if the transmittance $T(\lambda)$ of the non-vascular site portion is assumed as "1".

In addition, the light intensity $Os(\lambda)$ obtained by the measurement-purpose light receiving unit Sd which includes the transmitted light of the blood vessel 4 is expressed by $Os(\lambda)=P(\lambda) \cdot T(\lambda) \cdot S(\lambda)$. Based on these two expressions, the transmittance $T(\lambda)$ is obtained. In addition, the transmittance $T(\lambda)$ is a value relative to the transmittance of the non-vascular site 8.

(A-4-1) Light Emitting Method During Measurement

In the present embodiment, the light is emitted by the measurement-purpose light emitting unit Ld or the reference-purpose light emitting unit Lr so as to acquire the light receiving result for one time, while the plurality of light emitting patterns including the light emitting element which emits the light and the light emitting element which does not emit the light in the plurality of light emitting elements 53 inside the light emitting region R1 are switched. In FIG. 9, in order to facilitate understanding of the technique, the light emitting region R1 is provided with the three light emitting elements 53 in the vertical direction (Ys-direction) and the three light emitting elements 53 in the horizontal direction (Xs-direction). However, in the present embodiment, the light emitting region R1 is a region where every 15 light emitting elements 53 are respectively provided in both the vertical and horizontal directions. In the description herein, the light emitting region R1 is a region surrounding an outer periphery of the light emitting element 53 which emits the light in any one of the light emitting patterns. A boundary of the light emitting region R1 is located between the light emitting element 53 which emits the light in any one of the light emitting patterns and the light emitting element 53 which does not emit the light in any one of the light emitting patterns.

FIG. 10 is a schematic view illustrating a plurality of light emitting patterns P11 to P14 in the light emitting region R1 according to the present embodiment. In FIG. 10, in the light emitting elements 53 inside the light emitting region R1, the light emitting element 53 emitting the light is illustrated as a light emitting element 53on, and the light emitting element 53 which does not emit the light is illustrated as a light emitting element 53off. In the present embodiment, an emitting time of the light emitted by the measurement-purpose light emitting unit Ld so as to acquire the light receiving result for one time is 4 seconds. The light is emitted by the measurement-purpose light emitting unit Ld so as to acquire the light receiving result for one time, while the light emitting patterns are switched every 0.5 seconds. Specifically, the light emitting patterns are switched sequentially from the light emitting pattern P11 to the light emitting pattern P12, P13, and P14. Subsequent to the light emitting pattern P14, the light emitting pattern is switched to the light emitting pattern P11. That is, in the present embodiment, the plurality of light emitting patterns are all repeated every twice which is the same number of times. Characteristics and advantageous points of the plurality of light emitting patterns P11 to P14 will be described later.

(A-5) Calculation of Blood Glucose Level

Subsequently, based on the absorption spectrum, the blood glucose level is estimated and calculated using a calibration curve showing a relationship between a predetermined blood glucose level (glucose concentration in the blood) and absorbance. A technique itself for calculating the concentration of a predetermined component (glucose in the present embodiment) from this absorption spectrum is known. In the present embodiment, the known technique can be applied.

A3. Functional Configuration

FIG. 11 is a functional configuration diagram of the blood glucose level measurement device 10 according to the present embodiment. The blood glucose level measurement device 10 is configured to functionally include an operation input unit 110, a display unit 120, a sound output unit 130, a communication unit 140, an irradiation unit 210, an imaging unit 220, a control unit 300, and a storage unit 400.

The operation input unit 110 is an input device such as a button switch, a touch panel, and various sensors, and outputs an operation signal according to the operation to the control unit 300. The operation input unit 110 performs various instruction inputs such as instructions to start measurement of the blood glucose level. In FIG. 1, the operation switch 18 or the touch panel 16 corresponds to the operation input unit 110.

The display unit 120 is a display device such as a liquid crystal display (LCD), and performs various displays based on a display signal output from the control unit 300. The measurement result is displayed on the display unit 120. In FIG. 1, the touch panel 16 corresponds to the display unit 120.

The sound output unit 130 is a sound output device such as a speaker, and performs various sound outputs based on a sound signal output from the control unit 300. The sound output unit 130 outputs a notification sound for notifying the measurement start or the measurement completion of the blood glucose level, and occurrence of a low blood glucose level.

The communication unit 140 is a communication device such as a wireless communication device, a modem, a jack of a communication cable for wired communication, and a control circuit, and external communication is realized by being connected to a communication line. In FIG. 1, the communication device 20 corresponds to the communication unit 140.

The irradiation unit 210 has multiple light emitting elements 53 which are two-dimensionally arranged in a planar fashion. The light emitting layer 52 of the sensor module 50 illustrated in FIG. 2 corresponds to the irradiation unit 210. The arrangement position of the irradiation unit 210 (specifically, position coordinates of the respective light emitting elements 53 in the Xs-Ys orthogonal coordinate system) is stored as a light emitting element list 406 in the storage unit 400.

The imaging unit 220 has multiple light receiving elements 59 which are two-dimensionally arranged in a planar fashion. The light receiving layer 58 of the sensor module 50 illustrated in FIG. 2 corresponds to the imaging unit 220.

The arrangement position of the imaging unit 220 (specifically, position coordinates of the respective light receiving elements 59 in the Xs-Yx orthogonal coordinate system) is stored as a light receiving element list 408 in the storage unit 400.

For example, the control unit 300 is realized by a microprocessor such as a CPU or a graphics processing unit (GPU) or electronic components such as an application specific integrated circuit (ASIC) and an IC memory. Based on a predetermined program, data, or an operation signal output from the operation input unit 110, the control unit 300 performs various arithmetic processes, and controls the operation of the blood glucose level measurement device 10. In FIG. 1, the control board 30 corresponds to the control unit 300. In addition, the control unit 300 has a blood glucose level measurement unit 310, an irradiation control unit 342, and an imaging control unit 344. The irradiation control unit 342 selectively controls each of the plurality of light emitting elements 53 to emit the light. The imaging control unit 344 acquires the light quantity received from each of the plurality of light receiving elements 59.

The blood glucose level measurement unit 310 has a biological image acquisition unit 314, a vascular pattern acquisition unit 316, a vascular site selection unit 318, a measurement-purpose light receiving and emitting unit selection unit 320, a reference-purpose light receiving and emitting unit selection unit 322, an absorption spectrum calculation unit 324, and a component value calculation unit 326. The blood glucose level measurement unit 310 measures the glucose concentration, that is, the blood glucose level in the blood of the user 2.

The biological image acquisition unit 314 acquires a biological image of the user 2. Acquisition of the biological image is realized by appropriately using a biological image capturing technique in the known vein authentication technology. That is, the light emitting elements 53 are caused to simultaneously emit the light, and the light receiving elements 59 measure (image) the light. Then, a luminance image based on the light measurement result, that is, the biological image is generated. The biological image acquired by the biological image acquisition unit 314 is stored as biological image data 414 in the storage unit 400.

The vascular pattern acquisition unit 316 performs predetermined image processing on the biological image acquired by the biological image acquisition unit 314 so as to acquire a vascular pattern. Specifically, the image processing is realized by appropriately using a technique for identifying a vein pattern from the biological image in the known vein authentication technology. For example, reference luminance is compared for each pixel of the biological image, and each pixel is subjected to binary coded processing and filter processing. The pixel whose luminance is lower than the reference luminance indicates the blood vessel, and the pixel whose luminance is equal to or higher than the reference luminance indicates the non-vascular site. The vascular pattern acquired by the vascular pattern acquisition unit 316 is stored as vascular pattern data 416 in the storage unit 400.

Based on the vascular pattern acquired by the vascular pattern acquisition unit 316, the vascular site selection unit 318 selects the vascular site 6 indicating a predetermined selection condition, as the measurement target. Here, the vascular site 6 serving as the measurement target may be one or more. Each of the vascular sites 6 selected as the measurement target is stored as vascular site data 418 in the storage unit 400.

FIG. 12 illustrates an example of a data configuration of the vascular site data 418. The vascular site data 418 stores a vascular site ID 418a serving as identification information of the vascular site, a site pixel list 418b, center line position information 418c, a site length 418d which is a length in the longitudinal direction of the blood vessel, measurement-purpose light emitting unit data 418e, measurement-purpose light receiving unit data 418f, reference-purpose light emitting unit data 418g, and reference-purpose light receiving unit data 418h. The site pixel list 418b is a list of pixels (that is, the light receiving element 59) corresponding to the vascular site. The center line position information 418c is information on the position coordinates of the center line (center in the width direction of the blood vessel and a line extending along the longitudinal direction of the blood vessel) of the vascular site in the Xs-Ys orthogonal coordinate system.

The measurement-purpose light receiving and emitting unit selection unit 320 selects the measurement-purpose light emitting unit Ld and the measurement-purpose light receiving unit Sd for each of the vascular sites 6 serving as the measurement target. Specifically, one position on the center line of the vascular site 6 is selected as the measurement-purpose light emitting unit Ld in the Xs-Ys orthogonal coordinate system (that is, on the skin surface), and the measurement-purpose light receiving unit Sd which is separated from the measurement-purpose light emitting unit Ld by the predetermined distance W and which is located on the center line of the vascular site 6 is selected. A selection condition of the measurement-purpose light emitting unit Ld and the measurement-purpose light receiving unit Sd will be referred to as a first condition. The predetermined distance W is stored as optimum distance data 410 in the storage unit 400. For example, a selection method of one position on the center line of the vascular site 6 is determined using a substantially center position in the longitudinal direction of the vascular site 6. The selected measurement-purpose light emitting unit Ld is stored as measurement-purpose light emitting unit data 418e, and the selected measurement-purpose light receiving unit Sd is stored as measurement-purpose light receiving unit data 418f.

In a case where the measurement-purpose light emitting unit Ld and the measurement-purpose light receiving unit Sd which satisfy the above-described first condition are not present, it is determined whether or not the measurement-purpose light emitting unit Ld and the measurement-purpose light receiving unit Sd which similarly satisfy the above-described first condition are present at a position separated from the one position by a predetermined unit distance along the center line of the vascular site 6. Nevertheless, in a case where the measurement-purpose light emitting unit Ld and the measurement-purpose light receiving unit Sd which satisfy the above-described first condition are not present, this process is similarly repeated. In this manner, the measurement-purpose light emitting unit Ld and the Search and select measurement-purpose light receiving unit Sd are searched for and selected. The reference-purpose light emitting unit Lr is stored as the reference-purpose light emitting unit data 418g, and the selected reference-purpose light emitting unit Lr is stored as the reference-purpose light receiving unit data 418h.

Based on the measurement-purpose light emitting unit Ld and the measurement-purpose light receiving unit Sd which are set by the measurement-purpose light receiving and emitting unit selection unit 320, the reference-purpose light receiving and emitting unit selection unit 322 selects one position which is not located above the blood vessel 4, as the reference-purpose light emitting unit Lr, and selects the reference-purpose light receiving unit Sr which is separated from the reference-purpose light emitting unit Lr by the predetermined distance W and which is not located above the blood vessel 4. A selection condition of the reference-purpose light emitting unit Lr and the reference-purpose light receiving unit Sr will be referred to as a second condition.

In the present embodiment, as illustrated in FIG. 7, the reference-purpose light receiving unit Sr is selected in which the distance J between the measurement-purpose light emitting unit Ld and the reference-purpose light emitting unit Lr is 5 mm, and in which the straight line connecting the measurement-purpose light emitting unit Ld and the measurement-purpose light receiving unit Sd to each other and the straight line connecting the reference-purpose light emitting unit Lr and the reference-purpose light receiving unit Sr to each other are substantially parallel to each other. The above-described selection condition different from the first condition and the second condition will be referred to as a third selection condition. In a case where the reference-purpose light emitting unit Lr and the reference-purpose light receiving unit Sr which satisfy the second condition and the third condition are not present, the measurement-purpose light receiving and emitting unit selection unit 320 searches for and selects the measurement-purpose light emitting unit Ld and the measurement-purpose light receiving unit Sd.

The absorption spectrum calculation unit 324 generates an absorption spectrum for each of the vascular sites 6 serving as the measurement target. Specifically, based on the first light receiving result Q1 obtained from the measurement-purpose light receiving unit Sd and the second light receiving result Q2 obtained from the reference-purpose light receiving unit Sr, the transmittance T of each wavelength λ is calculated so as to generate the absorption spectrum. Furthermore, in a case where the plurality of vascular sites 6 serving as the measurement target are present, absorption spectra of the plurality of respective vascular sites 6 serving as the measurement targets are averaged so as to calculate an average absorption spectrum. The absorption spectrum calculated by the absorption spectrum calculation unit 324 is stored as absorption spectrum data 420 in the storage unit 400.

Based on the absorption spectrum calculated by the absorption spectrum calculation unit 324, the component value calculation unit 326 calculates the glucose concentration (that is, the blood glucose level) which indicates the blood concentration of a target blood component. In the present embodiment, the absorption spectrum is used for an analysis method such as a multiple regression analysis method, a principal component regression analysis method, a PLS regression analysis method, and an independent component analysis method. In a case where the plurality of vascular sites 6 serving as the measurement target are present, the blood glucose level is calculated from the average absorption spectrum obtained by averaging the absorption spectra of the respective vascular sites 6. The blood glucose levels calculated by the component value calculation unit 326 are accumulated and stored in the storage unit 400 as measured blood glucose level data 422 in association with the measurement time.

The storage unit 400 is a storage device such as a ROM, a RAM, and a hard disk, and stores programs and data for the control unit 300 to integrally control the blood glucose level measurement device 10. The storage unit 400 is used as a work region of the control unit 300, and temporarily stores calculation results obtained by the control unit 300 or operation data output from the operation input unit 110. In FIG. 1, the main memory or the measurement data memory mounted on the control board 30 corresponds to the storage unit 400. The storage unit 400 stores a system program 402, a blood glucose level measurement program 404, a light emitting element list 406, a light receiving element list 408, optimum distance data 410, biological image data 414, vascular pattern data 416, vascular site data 418, absorption spectrum data 420, and measured blood glucose level data 422.

A4. Biological Information Acquisition Method

FIG. 13 is a flowchart for describing a flow in a blood glucose level measurement process as the biological information acquisition method. The process is realized by the control unit 300 which performs the process according to the blood glucose level measurement program 404.

Referring to FIG. 13, the blood glucose level measurement unit 310 performs a measurement process for measuring the blood glucose level of the user. First, the biological image acquisition unit 314 of the blood glucose level measurement unit 310 sets the entire surface of the light emitting surface of the sensor module 50 (that is, a range including substantially all of the light emitting elements 53) as a light emitting range. The light emitting elements 53 within the light emitting range are caused to emit the light so as to obtain the biological image of the user (Step P120). Subsequently, the vascular pattern acquisition unit 316 acquires the vascular pattern viewed from the skin surface, based on the obtained biological image (Step P130). As a result, if the vascular pattern cannot be obtained (Step P140: NO), the process returns to Step P120.

If the vascular pattern is obtained (Step P140: YES), the vascular site selection unit 318 selects the vascular site 6 serving as the measurement target which satisfies the predetermined selection condition, based on the obtained vascular pattern (Step P150). Then, the measurement-purpose light receiving and emitting unit selection unit 320 selects the measurement-purpose light emitting unit Ld and the measurement-purpose light receiving unit Sd (Step P160). Next, the measurement-purpose light emitting unit Ld is caused to emit the light (Step P170), and the first light receiving result Q1 is obtained by the selected measurement-purpose light receiving unit Sd (Step P180).

Thereafter, the reference-purpose light receiving and emitting unit selection unit 322 selects the reference-purpose light emitting unit Lr and the reference-purpose light receiving unit Sr (Step P190). Next, the reference-purpose light emitting unit Lr is caused to emit the light (Step P200), and the second light receiving result Q2 is obtained by the selected reference-purpose light receiving unit Sr (Step P210). A predetermined time interval is set between the step of acquiring the first light receiving result (Step P180) and the step of acquiring the second light receiving result (Step P210). In the present embodiment, the interval for 5 seconds is set as the predetermined time interval.

Next, the absorption spectrum calculation unit 324 generates the absorption spectrum for the vascular site 6 by using the first light receiving result Q1 and the second light receiving result Q2 (Step P220). Furthermore, in a case where the plurality of vascular sites 6 serving as the measurement target are present, the absorption spectrum obtained by averaging the absorption spectra of the respective vascular sites 6 is calculated.

Thereafter, based on the absorption spectrum, the component value calculation unit 326 calculates the glucose concentration in the blood, that is, the blood glucose level (Step P230). Then, the calculated blood glucose levels are displayed on the display unit 120, and are accumulated and stored in association with the measurement time (Step P240). After a predetermined waiting time elapses (Step P250), the process returns to Step P120, and the subsequent blood glucose level is similarly measured.

A5. Operation Effect

A5-1. Operation Effect Using Light Emitting Pattern

In the biological information acquisition device 10 according to the present embodiment, the light is emitted by the measurement-purpose light emitting unit Ld or the reference-purpose light emitting unit Lr, while the plurality of light emitting patterns P11 to P14 (refer to FIG. 10) are switched. Therefore, according to the biological information acquisition device 10 in the present embodiment, in some cases, the light emitting element 53 emitting the light in a certain light emitting pattern may not emit the light in the other light emitting pattern. Accordingly, the light emitting element 53 is restrained from continuously emitting the light. Therefore, it is possible to restrain the light emitting element 53 from being degraded due to generated heat.

The following shows results indicating that the degradation of the light emitting element 53 is restrained by causing the measurement-purpose light emitting unit Ld to emit the light so as to acquire the light receiving result for one time while the plurality of light emitting patterns are switched. Specifically, the results are shown in which a light source lifespan in a case of using the light emitting pattern according to the present embodiment and other light emitting patterns is compared with that of a comparative example.

FIG. 14 is a schematic view illustrating light emitting patterns P21 to P23 which are different from those according to the present embodiment. In this form, the light is emitted while the light emitting patterns are switched approximately every 0.67 seconds. Specifically, the light emitting patterns are switched sequentially from the light emitting pattern P21 to the light emitting patterns P22 and P23. Subsequent to the light emitting pattern P23, the light emitting pattern is switched to the light emitting pattern P21. A plurality of the light emitting patterns P11 to P14 (refer to FIG. 10) used for the above-described embodiment will be collectively referred to as a lighting pattern A, and a plurality of the light emitting patterns P21 to P23 illustrated in FIG. 14 will be collectively referred to as a lighting pattern B.

FIG. 15 is a schematic view illustrating light emitting patterns P31 to P33 which are different from those according to the present embodiment. In this form, the light is emitted while the light emitting patterns are switched every 0.67 seconds approximately. Specifically, the light emitting patterns are switched sequentially from the light emitting pattern P31 to the light emitting patterns P32 and P33. Subsequent to the light emitting pattern P33, the light emitting pattern is switched to the light emitting pattern P31. A plurality of the light emitting patterns P31 to P33 illustrated in FIG. 15 will be collectively referred to as a lighting pattern C.

FIGS. 16 and 17 are schematic views illustrating a lighting pattern according to a comparative example. FIG. 16 is a schematic view illustrating a pattern P41 in which all of the light emitting elements 53 inside the light emitting region R1 are continuously lit. In addition, FIG. 17 is a schematic view illustrating a pattern P51 in which all of the light emitting elements 53 inside the light emitting region R1 are turned on and the pattern P51 in which all of the light emitting elements 53 inside the light emitting region R1 are not turned on. The patterns P51 and P52 illustrated in FIG. 17 are alternately switched every 2 seconds. The pattern P41 illustrated in FIG. 16 will be referred to as a lighting pattern D, and the patterns P51 and P52 illustrated in FIG. 17 will be collectively referred to as a lighting pattern E.

FIG. 18 illustrates a result obtained by measuring a light source lifespan in a case where the light emitting elements are turned on in each lighting pattern. The result of the light source lifespan shows a time until the light quantity of the light emitting element reaches 80% of the light quantity at a start time of an experiment. In addition, the OLED is used as the light emitting element. As a method of preparing the OLED, it is possible to refer to JP-A-2012-219078.

In Application Example 1 to Application Example 3 in which the light is emitted while the plurality of light emitting patterns including the light emitting element 53 which emits the light and the light emitting element 53 which does not emit the light are switched, it is understood from FIG. 18 that the light source lifespan is longer than that of Comparative Example 1 and Comparative Example 2 in which the light emitting patterns are not switched. That is, based on this result, it is understood that the degradation of the light emitting element 53 can be restrained by emitting the light so as to acquire the light receiving result for one time while switching the plurality of light emitting patterns.

In the lighting patterns A, B, and C (refer to FIGS. 10, 14, and 15), the light emitting element which emits the light in the light emitting pattern before being switched does not emit the light in the light emitting pattern after being switched. In this manner, the degradation of the light emitting element 53 can be restrained.

In addition, in the lighting patterns A, B, and C (refer to FIGS. 10, 14, and 15), in all of the light emitting patterns, the light emitting elements 53, the light emitting elements 53off which does not emit the light is present in the light emitting elements 53 adjacent to the light emitting elements 53on which emits the light. In this manner, the heat generated by the light emitting element 53on which emits the light is diffused to the adjacent light emitting element 53off which does not emit the light, thereby enabling the heat to be radiated. Therefore, the degradation of the light emitting element 53 can be restrained.

In addition, in all of the light emitting patterns serving as the lighting pattern A (refer to FIG. 10), any one of the light emitting elements 53 adjacent to the light emitting element 53on which emits the light is the light emitting element 53off which does not emit the light. In this manner, it is possible to more efficiently radiate the heat generated by the light emitting element 53on which emits the light. Therefore, the degradation of the light emitting element 53 can be restrained.

In addition, in the lighting patterns A, B, and C (refer to FIGS. 10, 14, and 15), the light emitting element 53 which emits the light in any one of the light emitting patterns does not emit the light in the other light emitting patterns. Therefore, the heat generated by the light emitting element 53on which emits the light can be radiated while the light emitting element 53 does not emit the light. Therefore, it is possible to restrain the heat from being locally accumulated.

In addition, in the lighting patterns B and C (refer to FIGS. 14 and 15), the light emitting element located at a position point-symmetric with respect to the center of the light emitting unit L emits the light, and the light emitting element located at a position line-symmetric with respect to a line passing through the light emitting unit L emits the light. Therefore, it is possible to restrain a variation in the light quantity between the light emitting patterns. As a result, the biological information can be accurately acquired.

In addition, in all of the lighting patterns A, B, and C (refer to FIGS. 10, 14, and 15), the light emitting elements 53, the number of which is a predetermined number or more, emit the light. Specifically, in all of the lighting patterns A, B, and C (refer to FIGS. 10, 14, and 15), 10% or more of the light emitting elements 53 in the sum of the light emitting elements included inside the light emitting region R1 emit the light. Therefore, compared to a case where the light emitting elements 53, the number of which is smaller than the predetermined number, emit the light, the biological information acquisition device 10 according to the present embodiment can obtain sufficient light emitting intensity. As a result, according to the biological information acquisition device 10 in the present embodiment, the biological information can be accurately acquired. It is more preferable that the predetermined number is 20% of the sum of the light emitting elements included inside the light emitting region R1, and it is much more preferable that the predetermined number is 30% of the sum of the light emitting elements included inside the light emitting region R1.

Since the heat generation of the light emitting element 53 is restrained, the heat can be restrained from being transferred to the living body wearing the biological information acquisition device 10. Therefore, it is possible to restrain a possibility of a low-temperature burn of the living body which may be caused by the heat generation of the light emitting element 53. In addition, since the heat generation of the light emitting element 53 is restrained, it is possible to restrain temperature rising of the biological information acquisition device 10 itself. Accordingly, it is also possible to restrain accuracy of the biological information acquisition device 10 from being degraded due to a temperature drift. Furthermore, since the living body is a scatterer of the light, the received light quantity is small. Therefore, it is necessary to increase the light emitting power. In particular, when the concentration of glucose in the blood is measured, it is preferable to further increase the light emitting power than that when the vascular position is acquired.

A5-2. Additional Operation Effect

In the biological information acquisition device 10 according to the present embodiment, the measurement-purpose light emitting unit Ld is selected, based on the vascular position. In this manner, the light emitting unit L suitable for acquiring the biological information relating to the blood vessel can be selected as the measurement-purpose light emitting unit Ld. Therefore, according to the biological information acquisition device 10 in the present embodiment, the biological information relating to the blood vessel can be accurately acquired.

In addition, in the biological information acquisition device 10 according to the present embodiment, the OLED is used as the light emitting element 53. Glass transition temperature of an organic material used for the OLED is generally approximately 90° C. to 130° C. However, there is a possibility that the temperature of the OLED may reach the glass transition temperature due to the heat generated by the light emission. In a case where the temperature of the OLED reaches the glass transition temperature, light emitting efficiency of the OLED may become poor. However, according to the present embodiment, it is possible to restrain the degradation of the light emitting element 53 by radiating the heat generated in the light emitting element. Therefore, the OLED can be used.

In the biological information acquisition device 10 according to the present embodiment, the light source (the measurement-purpose light emitting unit Ld) in the first light receiving result is different from the light source in the second light receiving result. Therefore, it is possible to select the measurement-purpose light emitting unit Ld which is located above the blood vessel, and it is possible to select the reference-purpose light emitting unit Lr which is not located above the blood vessel. As a result, in a case of the first light receiving result obtained by causing the measurement-purpose light receiving unit Sd located above the blood vessel to receive the light emitted from the measurement-purpose light emitting unit Ld located above the blood vessel, the emitted light passes through the blood vessel at a high rate. Accordingly, the first light receiving result includes a lot of information relating to the blood vessel and the blood inside the blood vessel. On the other hand, in a case of the second light receiving result obtained by causing the reference-purpose light receiving unit Sr which is not located above the blood vessel to receive the light emitted from the reference-purpose light emitting unit Lr which is not located above the blood vessel, the emitted light passes through the blood vessel at a low rate. Accordingly, the second light receiving result includes less information relating to the blood vessel or the blood inside the blood vessel. The biological information is acquired using the first light receiving result and the second light receiving result in this way. Therefore, according to the biological information acquisition device 10 in the present embodiment, the biological information can be accurately acquired.

In addition, in the biological information acquisition device 10 according to the present embodiment, the straight line connecting the measurement-purpose light emitting unit Ld and the measurement-purpose light receiving unit Sd to each other and the straight line connecting the reference-purpose light emitting unit Lr and the reference-purpose light receiving unit Sr are substantially parallel to each other. In addition, the distance between the measurement-purpose light emitting unit Ld and the reference-purpose light emitting unit Lr is 6 mm or shorter. Therefore, a structure of the living body in a light path where the light emitted by the measurement-purpose light emitting unit Ld moves forward to the measurement-purpose light receiving unit Sd approximates to a structure of the living body in a light path where the light emitted by the reference-purpose light emitting unit Lr moves forward to the reference-purpose light receiving unit Sr, except that the emitted light does not pass through the vascular site 6. Therefore, according to the biological information acquisition device 10 in the present embodiment, the biological information can be acquired using the first light receiving result and the second light receiving result. Accordingly, the biological information can be accurately acquired.

In addition, in the biological information acquisition device 10 according to the present embodiment, as a partial region of the light receiving and emitting region, the light emitting region R1 having a prescribed shape and size is selected, and the plurality of light emitting elements 53 inside the selected light emitting region R1 are caused to emit the light as the measurement-purpose light emitting unit Ld or the reference-purpose light emitting unit Lr. In this way, the light emitting unit L according to the present embodiment is formed from the plurality of light emitting elements 53. Therefore, compared to a case where one light emitting unit is formed from one light emitting element, the biological information acquisition device 10 according to the present embodiment can obtain sufficient light emitting intensity. As a result, according to the biological information acquisition device 10 in the present embodiment, the biological information can be accurately acquired.

Similarly, in the biological information acquisition device 10 according to the present embodiment, as a partial region of the light receiving and emitting region, the light receiving region R2 having a prescribed shape and size is selected, and the plurality of light receiving elements 59 inside the selected light receiving region R2 are caused to receive the light as the measurement-purpose light receiving unit Sd or the reference-purpose light receiving unit Sr. In this way, the light receiving unit S according to the present embodiment is formed from the plurality of light receiving elements 59. Therefore, compared to a case where one light receiving unit is formed from one light receiving element, the biological information acquisition device 10 according to the present embodiment can obtain the sufficient light receiving amount. As a result, according to the biological information acquisition device 10 in the present embodiment, the biological information can be accurately acquired.

In addition, in the biological information acquisition device 10 according to the present embodiment, one light emitting unit L is formed from a group of the plurality of smaller light emitting elements 53. Accordingly, a position of the light emitting unit L can be selected in pitch unit of the small light emitting element 53. Therefore, according to the biological information acquisition device 10 in the present embodiment, the light emitting unit L can be more freely selected.

Similarly, in the biological information acquisition device 10 according to the present embodiment, one light receiving unit S is formed from a group of the plurality of smaller light receiving elements 59. Accordingly, a position of the light receiving unit S can be selected in pitch unit of the small light receiving element 59. Therefore, according to the biological information acquisition device 10 in the present embodiment, the light receiving unit S can be more freely selected.

In the biological information acquisition method according to the present embodiment, the predetermined time is set between the step of acquiring the first light receiving result (Step P180 (refer to FIG. 13)) and the step of acquiring the second light receiving result (Step P210). Therefore, it is possible to restrain the reference-purpose light receiving unit Sr from receiving light emitted by the measurement-purpose light emitting unit Ld, or to restrain the measurement-purpose light receiving unit Sd from receiving the light emitted by the reference-purpose light emitting unit Lr. As a result, according to the biological information acquisition method of the present embodiment, the biological information can be accurately acquired.

B. Second Embodiment

The second embodiment is different from the first embodiment in that a selection method of the reference-purpose light emitting unit Lr and the reference-purpose light receiving unit Sr is different. However, the other configurations are the same as those according to the first embodiment.

In a biological information acquisition device 10A according to a second embodiment, a position where the luminance when the biological image is acquired falls within the top 10% inside the whole light receiving and emitting region is selected as the reference-purpose light emitting unit Lr and the reference-purpose light receiving unit Sr. A distance between the reference-purpose light emitting unit Lr and the reference-purpose light receiving unit Sr is set to the predetermined distance W which is the same as that according to the first embodiment.

As described above, the blood vessel is more likely to absorb near-infrared rays than the non-blood vessel portion. Accordingly, in the acquired biological image, the vascular portion has lower luminance than the non-blood vessel portion. In addition, capillary blood vessels pass through all over the human body. Therefore, there is a high possibility that the blood vessel including the capillary blood vessels may not exist at a position where all ranks of the luminance fall within the top 10% when the biological image is acquired. This position is selected as the reference-purpose light emitting unit Lr and the reference-purpose light receiving unit Sr. In this manner, the second light receiving result obtained by the reference-purpose light receiving unit Sr from the light emitted by the reference-purpose light emitting unit Lr has less information relating to the blood vessel or the blood in the blood vessel. As a result, according to the biological information acquisition device 10 in the present embodiment, the biological information can be accurately acquired.

C. Modification Example

The present invention is not limited to the above-described application examples or modification example, and can be embodied in various aspects within the scope not departing from the gist of the present invention. For example, the following modifications can be adopted.

C1. Modification Example 1

In the above-described embodiments, the plurality of light emitting patterns P11 to P14 illustrated in FIG. 10 are used. However, the present invention is not limited thereto. For example, the light emitting pattern may be used as follows.

FIG. 19 is a schematic view illustrating light emitting pattern P61 to P64 which are different from those according to the present embodiment. In this form, the emitting time of the light emitted by the measurement-purpose light emitting unit Ld so as to acquire the light receiving result for one time is 4 seconds. The light is emitted by the measurement-purpose light emitting unit Ld so as to acquire the light receiving result for one time, while the light emitting patterns are switched every 0.5 seconds. Specifically, the light emitting patterns are switched sequentially from the light emitting pattern P61 to the light emitting patterns P62, P63, and P64. Subsequent to the light emitting pattern P64, the light emitting pattern is switched to the light emitting pattern P61. That is, in this form, the plurality of light emitting patterns are all repeated every twice which is the same number of times.

FIG. 20 is a schematic view illustrating light emitting patterns P71 to P73 which are different from those according to the present embodiment. In this form, the emitting time of the light emitted by the measurement-purpose light emitting unit Ld so as to acquire the light receiving result for one time is 4 seconds. The light is emitted by the measurement-purpose light emitting unit Ld so as to acquire the light receiving result for one time, while the light emitting patterns are switched every 0.67 seconds approximately. Specifically, the light emitting patterns are switched sequentially from the light emitting pattern P71 to the light emitting patterns P72 and P73. Subsequent to the light emitting pattern P73, the light emitting pattern is switched to the light emitting pattern P71. That is, in this form, the plurality of light emitting patterns are all repeated every twice which is the same number of times.

FIG. 21 is a schematic view illustrating light emitting patterns P81 and P82 which are different from those according to the present embodiment. In this form, the emitting time of the light emitted by the measurement-purpose light emitting unit Ld so as to acquire the light receiving result for one time is 4 seconds. The light is emitted by the measurement-purpose light emitting unit Ld so as to acquire the light receiving result for one time, while the light emitting patterns are switched every one second. Specifically, the light emitting pattern P81 and the light emitting pattern P82 are alternately switched in this order. That is, in this form, the plurality of light emitting patterns are all repeated every twice which is the same number of times.

In the light emitting patterns illustrated in FIGS. 20 and 21, the light emitting element which emits the light in the light emitting pattern before being switched does not emit the light in the light emitting pattern after being switched. In addition, in the light emitting patterns illustrated in FIGS. 19, 20, and 21, in all of the light emitting patterns, the light emitting element 53off which does not emit the light exists in the light emitting element 53 adjacent to the light emitting element 53on which emits the light.

In addition, in the light emitting patterns illustrated in FIGS. 20 and 21, the light emitting element 53 which emits the light in any one of the light emitting patterns does not emit the light in the other light emitting pattern. In addition, in the light emitting patterns illustrated in FIGS. 19, 20, and 21, the light emitting element located at a point point-symmetric with respect to the center of the light emitting unit L emits the light, and the light emitting element located at a position line-symmetric with respect to the line passing through the center of the light emitting unit L does not emit the light.

It is preferable that a set of the plurality of light emitting patterns used to obtain the light receiving result for one time has one or more characteristic points described below.

<Characteristic Point 1> In the set of the plurality of light emitting patterns, the light emitting elements 53 which emit the light are at least partially different from each other.

<Characteristic Point 2> The light emitting elements 53 which emit the light in the respective light emitting patterns are located at positions point-symmetric with respect to the center inside the light emitting unit 53 (inside the light emitting region R1).

<Characteristic Point 3> The light emitting elements 53 which emit the light in the respective light emitting patterns are located at positions line-symmetric with respect to the line passing through the center inside the light emitting unit 53 (inside the light emitting region R1).

<Characteristic Point 4> In the set of the plurality of light emitting patterns, the light emitting element 53 which emits the light in an optional light emitting pattern does not emit the light in a light emitting pattern subsequent to the optional light emitting pattern.

<Characteristic Point 5> In the respective light emitting patterns, the other four light emitting elements 53 located at four positions in the vicinity of the light emitting element 53 which emits the light do not emit the light.

<Characteristic Point 6> In the respective light emitting patterns, the other eight light emitting elements 53 located at eight positions in the vicinity of the light emitting element 53 which emits the light do not emit the light.

<Characteristic Point 7> In the set of the plurality of light emitting patterns, with regard to individual light emitting elements 53 which emit the light, the numbers of light emitting times N (N is an integer of 1 or more) obtained by summing up the set of the plurality of light emitting patterns are the same as each other.

<Characteristic Point 8> With regard to all of the light emitting elements 53 inside the light emitting unit 53, the number of light emitting times obtained by summing up the set of the plurality of light emitting patterns is at least once or more.

<Characteristic Point 9> The numbers of using times M (M is an integer of 1 or more) of the respective light emitting patterns in the set of the plurality of light emitting patterns are the same as each other each other.

The set of the light emitting pattern P11 to P14 illustrated in FIG. 10 has the above-described characteristic points 1, 3, 4, 5, 6, 7, 8, and 9. If the set of the light emitting pattern P11 to P14 is used, it is possible to prevent the same light emitting elements 53 from continuously emitting the light. Therefore, it is possible to restrain the degradation caused by the heat generation of the light emitting element 53.

C2. Modification Example 2

In the above-described embodiments, the blood glucose level is acquired as the biological information. However, the present invention is not limited thereto. For example, oxygen saturation in the blood of the living body of the user may be acquired as the biological information. The oxygen saturation means a ratio of hemoglobin bound to oxygen in the hemoglobin contained in a red blood cell. In a case of the hemoglobin contained in the blood, absorbance of red light is different from absorbance of infrared light depending on whether or not the hemoglobin is bound to oxygen. Therefore, for example, the oxygen saturation can be acquired by using a plurality of element sets having different light emitting wavelength and light receiving wavelength, such as elements which emit the red light or receive the red light, and elements which emit the infrared light or receive the infrared light.

In addition, according to the above-described embodiment, the present invention is applied to the device for acquiring the blood glucose level. However, the present invention is not limited thereto. For example, the device to which the present invention is applicable includes a skin diagnosis device, a body fat measurement device, an in-vivo fluorescent light source observation device, a vein authentication device, an infrared scanner device, a skin cancer diagnosis device, a pupil observation device, and a blood vessel observation device. The light emitting unit according to the present invention is applicable to a light source of these devices.

C3. Modification Example 3

In the above-described embodiments, the light is emitted so as to acquire the light receiving result, while the plurality of light emitting patterns are switched. However, the present invention is not limited thereto. That is, the light may be emitted when the vascular position is specified, while the plurality of light emitting patterns are switched. However, in order to acquire more vascular information (glucose concentration or oxygen saturation), the light receiving unit needs to receive much more light transmitted through the living body. Accordingly, it is preferable that the light emitting amount of the light in acquiring the light receiving result is more than the light emitting amount of the light when the vascular position is specified. Therefore, it is preferable that the light is emitted so as to acquire the light receiving result, while the plurality of light emitting patterns are switched.

C4. Modification Example 4

In the above-described embodiments, after the step of acquiring the first light receiving result Q1 is performed (Step P180), the step of acquiring the second light receiving result Q2 is performed (Step P210). However, the present invention is not limited thereto. After the step of acquiring the second light receiving result Q2, the step of acquiring the first light receiving result Q1 may be performed.

C5. Modification Example 5

In the above-described embodiments, the position which is not located above the blood vessel 4 is selected as the reference-purpose light emitting unit Lr, and the reference-purpose light receiving unit Sr which is separated from the reference-purpose light emitting unit Lr by the predetermined distance W and which is not located above the blood vessel 4 is selected. However, the invention is not limited thereto. That is, in addition to the above-described condition, a condition may be added which does not include the position located above the blood vessel between the reference-purpose light emitting unit Lr and the reference-purpose light receiving unit Sr. In this manner, in a case of the second light receiving result obtained by the reference-purpose light receiving unit Sr, the emitted light passes through the blood vessel at a low rate. Accordingly, the second light receiving result has less information relating to the blood vessel or the blood inside the blood vessel. As a result, the biological information can be accurately acquired.

C6. Modification Example 6

In the above-described embodiments, after the light emitting unit L and the light receiving unit S are selected (for example, Step P160), the light emitting unit L is caused to emit the light (for example, Step P170). However, the present invention is not limited thereto. After the light emitting unit L is caused to emit the light, the light receiving unit S may be selected.

C7. Modification Example 7

In the above-described embodiments, after the light emitting unit L is selected, the light receiving unit S separated from the light emitting unit L by the predetermined distance W is selected. However, the present invention is not limited thereto. After the light receiving unit S is selected, the light emitting unit L separated from the light receiving unit S by the predetermined distance W may be selected. In addition, as the position of the light emitting unit L and the light receiving unit S, it is possible to employ various positions other than the position in the example illustrated in FIG. 7.

The elements other than the elements described in the independent claims among the configuration elements in the above-described embodiments and modification examples are additional elements, and may be appropriately omitted.

REFERENCE SIGNS LIST

1: light emitting element
2: user
4: target blood vessel
5a: bifurcated/joined site
5b: image end portion
6: vascular site
8: non-vascular site
10: biological information acquisition device
10A: biological information acquisition device
12: main body case
14: fixing band
16: touch panel
18: operation switch
20: communication device
22: memory card
24: reader/writer
26: battery
30: control board
50: sensor module
52: light emitting layer
53 (53on, 53off): light emitting element
54: light blocking layer
56: spectral layer
58: light receiving layer
59: light receiving element
110: operation input unit
120: display unit
130: sound output unit
140: communication unit
210: irradiation unit
220: imaging unit
300: control unit
310: blood glucose level measurement unit
314: biological image acquisition unit
316: vascular pattern acquisition unit
318: vascular site selection unit
320: measurement-purpose light receiving and emitting unit selection unit
322: reference-purpose light receiving and emitting unit selection unit
324: absorption spectrum calculation unit
326: component value calculation unit
342: irradiation control unit
344: imaging control unit
400: storage unit
402: system program
404: blood glucose level measurement program
406: light emitting element list
408: light receiving element list
410: optimum distance data
414: biological image data
416: vascular pattern data
418: vascular site data
418a: vascular site ID
418b: site pixel list
418c: center line position information
418d: site length
418e: measurement-purpose light emitting unit data
418f: measurement-purpose light receiving unit data
418g: reference-purpose light emitting unit data
418h: reference-purpose light receiving unit data
420: absorption spectrum data
422: measured blood glucose level data
L: light emitting unit
Ld: measurement-purpose light emitting unit
Lr: reference-purpose light emitting unit
O: light intensity
Or: light intensity
Os: light intensity P11 to P14, P21 to P23, P31 to P33, P61 to P64, P71 to P73, P81 to P82: light emitting pattern
P41, P51 to P52: pattern
A, B, C, D, E: lighting pattern
P4: vascular pattern
Q1: first light receiving result
Q2: second light receiving result
R1: light emitting region
R2: light receiving region
S: light receiving unit
Sd: measurement-purpose light receiving unit
Sr: reference-purpose light receiving unit
T: transmittance
W: predetermined distance

The invention claimed is:

1. A biological information acquisition device comprising:
   a light emitting layer that is formed from a plurality of light emitting elements so as to emit light to a living body;
   a light receiving layer that receives the light transmitted through the living body; and
   a processor that controls the light emitting layer and the light receiving layer,
   wherein the processor receives a light receiving result by causing the light receiving layer to receive the light emitted from the light emitting layer, and obtains biological information by using the light receiving result, and
   wherein the light is emitted from the light emitting layer so as to receive the light receiving result for one time, while a plurality of light emitting patterns are switched between the light emitting element which emits the light and the light emitting element which does not emit the light in the plurality of light emitting elements.

2. The biological information acquisition device according to claim 1, further comprising:
   a plurality of the light emitting layers,
   wherein the processor specifies a vascular position of the living body by causing at least one of the plurality of light emitting layers to emit the light, and
   wherein based on the vascular position, the light is emitted from the light emitting layer in the plurality of light emitting layers so as to receive the light receiving result for the one time.

3. The biological information acquisition device according to claim 1,
   wherein when the light is emitted from the light emitting layer so as to receive the light receiving result for the one time, the respective light emitting patterns of the plurality of light emitting patterns are all repeated the same number of times.

4. The biological information acquisition device according to claim 1,
   wherein the light emitting elements emitting the light in the respective light emitting patterns of the plurality of light emitting patterns are located at positions which are point-symmetric with respect to a center of the light emitting layer or which are line-symmetric with respect to a line passing through the center.

5. The biological information acquisition device according to claim 1,
   wherein in the respective light emitting patterns of the plurality of light emitting patterns, the light emitting element which does not emit the light is present in the light emitting elements adjacent to the light emitting element which emits the light.

6. The biological information acquisition device according to claim 1,
   wherein in the plurality of light emitting patterns, the light emitting element which emits the light in one light emitting pattern does not emit the light in another light emitting pattern subsequent to the one light emitting pattern.

7. The biological information acquisition device according to claim 1,
   wherein the light emitting layer emits the light including a near infrared ray having a wavelength of 0.7 μm to 2.5 μm.

8. The biological information acquisition device according to claim 1,
   wherein in the plurality of light emitting patterns, a number of light emitting elements emits light, the number being equal to or greater than a predetermined number.

9. The biological information acquisition device according to claim 1,
   wherein the biological information includes glucose concentration in blood of the living body.

10. The biological information acquisition device according to claim 1,
    wherein the biological information includes oxygen saturation in blood of the living body.

11. The biological information acquisition device according to claim 1,
    wherein an OLED is used as the light emitting element.

12. A biological information acquisition method of acquiring biological information by using a biological information acquisition device including a light emitting layer that is formed from a plurality of light emitting elements so as to emit light to a living body, and a light receiving layer that receives the light transmitted through the living body, the method comprising:
    a step of receiving a light receiving result by causing the light receiving layer to receive the light emitted from the light emitting layer; and
    a step of obtaining the biological information by using the light receiving result,
    wherein the light is emitted from the light emitting layer so as to receive the light receiving result for one time, while a plurality of light emitting patterns are switched between the light emitting element which emits the light and the light emitting element which does not emit the light in the plurality of light emitting elements.

* * * * *